US012009067B2

(12) United States Patent
Eteminan et al.

(10) Patent No.: US 12,009,067 B2
(45) Date of Patent: *Jun. 11, 2024

(54) OFFLINE MODE IN A MOBILE-NATIVE CLINICAL TRIAL OPERATIONS SERVICE SUITE

(71) Applicant: Laboratory Corporation of America Holdings, Burlington, NC (US)

(72) Inventors: Isaac Eshagh Eteminan, Rancho Santa Fe, CA (US); James William Bishop, Jr., Reno, NV (US); Marco Carosi, Rome (IT); Alessandro Salimbeni, Rome (IT)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/805,683

(22) Filed: Feb. 28, 2020

(65) Prior Publication Data
US 2020/0202985 A1 Jun. 25, 2020

Related U.S. Application Data

(63) Continuation-in-part of application No. 16/778,665, filed on Jan. 31, 2020, and a continuation-in-part of
(Continued)

(51) Int. Cl.
*G16H 10/20* (2018.01)
*G16H 40/67* (2018.01)
*G16H 80/00* (2018.01)

(52) U.S. Cl.
CPC ............ *G16H 10/20* (2018.01); *G16H 40/67* (2018.01); *G16H 80/00* (2018.01)

(58) Field of Classification Search
CPC .......................... H04L 67/1095; H04L 67/42
See application file for complete search history.

(56) References Cited

U.S. PATENT DOCUMENTS 8,397,161 B1 3/2013 Shah et al.
9,075,583 B1 * 7/2015 Cutter ...................... G06F 8/20
(Continued)

OTHER PUBLICATIONS

CIAOPS, Offline file conflicts with SharePoint Online, 2017 (Year: 2017).*
(Continued)

*Primary Examiner* — Evangeline Barr
*Assistant Examiner* — Anne-Marie K Alderson
(74) *Attorney, Agent, or Firm* — Kilpatrick Townsend & Stockton LLP

(57) ABSTRACT

A trial operations service suite system and method in a clinical trial operations system with a patient portal providing patient-directed access to clinical trial operation services, a clinician portal providing clinician-directed access to the clinical trial operation service, and a coordinator portal providing coordinator-directed access to the clinical trial operation services, the coordinator portal also providing access to a trial design service wherein the trial design service is configured to allow a coordinator user to at least one of design, create, establish, and deploy a trial protocol and a participant interaction procedure, and a synchronization capability, synchronizing when online, information collected while a portal-supporting application is offline.

19 Claims, 12 Drawing Sheets

Related U.S. Application Data application No. 16/100,094, filed on Aug. 9, 2018, and a continuation-in-part of application No. 16/100,078, filed on Aug. 9, 2018.

(56) References Cited

U.S. PATENT DOCUMENTS

| | | | |
|---|---|---|---|
| 11,594,307 B2 | 2/2023 | Eteminan et al. | |
| 2003/0158947 A1* | 8/2003 | Bloch | G06F 16/9574 709/227 |
| 2003/0208378 A1* | 11/2003 | Thangaraj | G16H 30/40 705/2 |
| 2004/0006553 A1 | 1/2004 | de Vries et al. | |
| 2004/0024616 A1 | 2/2004 | Spector et al. | |
| 2006/0224421 A1* | 10/2006 | St. Ores | A61B 5/0031 705/4 |
| 2007/0067189 A1 | 3/2007 | Boris et al. | |
| 2007/0168916 A1 | 7/2007 | Dahlin et al. | |
| 2008/0071575 A1 | 3/2008 | Climax et al. | |
| 2009/0228542 A1* | 9/2009 | Meijer | G06F 9/505 709/201 |
| 2009/0313045 A1 | 12/2009 | Boyce | |
| 2011/0125448 A1 | 5/2011 | Jung | |
| 2012/0259647 A1 | 10/2012 | Syed et al. | |
| 2013/0185096 A1 | 7/2013 | Giusti et al. | |
| 2014/0108054 A1 | 4/2014 | Udani | |
| 2014/0142984 A1 | 5/2014 | Wright et al. | |
| 2014/0201138 A1 | 7/2014 | Dorman et al. | |
| 2014/0340219 A1* | 11/2014 | Russell | G08B 29/188 340/539.12 |
| 2015/0331997 A1 | 11/2015 | Joao | |
| 2016/0110523 A1 | 4/2016 | Francois | |
| 2016/0147951 A1 | 5/2016 | Francois et al. | |
| 2016/0261705 A1* | 9/2016 | Lewandowski | H04L 67/1095 |
| 2017/0039324 A1* | 2/2017 | Francois | G16H 50/30 |
| 2017/0041205 A1* | 2/2017 | Rangel | G06F 13/385 |
| 2017/0161313 A1* | 6/2017 | Ritter | G06F 16/2365 |
| 2018/0174675 A1 | 6/2018 | Roy et al. | |
| 2018/0367506 A1* | 12/2018 | Ford | H04W 12/06 |
| 2019/0012434 A1 | 1/2019 | Frazier | |
| 2019/0026786 A1 | 1/2019 | Khoury et al. | |

OTHER PUBLICATIONS

Flowable Enterprise Documentation (documentation.flowable.com); Flowable Design/Process Editor; Apr. 8, 2013 (Year: 2013).*

NIH website, brics.cit.nih.gov/intro, "Introducing BRICS", Accessed via Wayback Machine Oct. 27, 2015 (Year: 2015).*

U.S. Appl. No. 16/778,665, Non-Final Office Action, dated May 7, 2021, 32 pages.

U.S. Appl. No. 16/100,078, Final Office Action, dated Jan. 14, 2021, 59 pages.

U.S. Appl. No. 16/100,078, Non-Final Office Action, dated May 11, 2020, 48 pages.

U.S. Appl. No. 16/100,094, Final Office Action, dated Jan. 14, 2021, 53 pages.

U.S. Appl. No. 16/100,094, Non-Final Office Action, dated May 11, 2020, 48 pages.

U.S. Appl. No. 16/100,078, Non-Final Office Action, dated Nov. 22, 2021, 20 pages.

U.S. Appl. No. 16/100,094, Non-Final Office Action, dated Nov. 22, 2021, 15 pages.

U.S. Appl. No. 16/778,665, Final Office Action, dated Oct. 25, 2021, 36 pages.

U.S. Appl. No. 16/818,634, Non-Final Office Action, dated Oct. 25, 2021, 25 pages.

U.S. Appl. No. 16/100,078, Final Office Action, dated Jun. 7, 2022, 15 pages.

U.S. Appl. No. 16/100,078, Non-Final Office Action, dated Dec. 23, 2022, 43 pages.

U.S. Appl. No. 16/100,094, Final Office Action, dated Jun. 7, 2022, 13 pages.

U.S. Appl. No. 16/100,094, Non-Final Office Action, dated Dec. 19, 2022, 38 pages.

U.S. Appl. No. 16/778,665, Final Office Action, dated Jan. 27, 2023, 34 pages.

U.S. Appl. No. 16/778,665, Non-Final Office Action, dated Jun. 9, 2022, 35 pages.

U.S. Appl. No. 16/818,634, Final Office Action, dated May 11, 2022, 10 pages.

U.S. Appl. No. 16/818,634, Notice of Allowance, dated Oct. 21, 2022, 8 pages.

* cited by examiner

OFFLINE MODE IN A MOBILE-NATIVE CLINICAL TRIAL OPERATIONS SERVICE SUITE

CROSS-REFERENCE TO RELATED APPLICATIONS

This application is a continuation-in-part of U.S. patent application Ser. No. 16/778,655, filed on Jan. 31, 2020, which is a continuation-in-part of U.S. patent application Ser. No. 16/100,0078, filed on Aug. 9, 2018, and U.S. patent application Ser. No. 16/100,994, which was also filed on Aug. 9, 2018, and claims the benefits thereof, the contents of each of which are incorporated herein by reference.

FIELD

This invention relates to clinical trial operations. More particularly, it relates to an offline mode for an automated service suite used by patients and/or doctors for clinical trial operations.

BACKGROUND

Healthcare applications of information and communication technology are growing rapidly. In the clinical trial arena, there is a need for clinical trial operations system(s) for various participants and relevant information in an efficient, secure, appropriately anonymized (also referred to as de-identified) manner that is more or less automated and convenient.

A significant aspect of the disclosed mobile-native clinical trial operations service suite is its distributed nature, wherein the web and mobile device applications interact with the service suite via a network. However, web and mobile device applications do not always have network connectivity, and therefore cannot always interact in real time with the service suite. Further, the service suite may on occasion be unavailable for interaction, whether because its network connectivity is compromised or for some other reason. Rather than disable the applications entirely, it is preferable to provide them in advance—that is, while they are connected—with a copy of the workflows and screens to use when a network connection is not available. What is needed, then, is an offline mode capability.

SUMMARY

Broadly, some embodiments enhance a mobile-native clinical trial operations service suite so that web and mobile device applications may continue to perform their user interaction and data collection functions while offline—that is, unable to communicate with the corresponding service suite—and then forward any collected data to the service suite at a later time when connectivity has been restored.

In one aspect of the disclosed embodiment(s), a trial operations service suite in a clinical trial operations system is provided, comprising: a patient portal providing patient-directed access to clinical trial operation services; a clinician portal providing clinician-directed access to the clinical trial operation services; and a coordinator portal providing coordinator-directed access to the clinical trial operation services, the coordinator portal also providing access to a trial design service wherein the trial design service is configured to allow a coordinator user to at least one of design, create, establish, and deploy a trial protocol and a participant interaction procedure; and a synchronization capability, synchronizing when online, information collected while a portal-supporting application is offline.

In another aspect of the disclosed embodiment(s), the above trial operations service is described, wherein the synchronization service synchronizes information between the clinician portal and a clinician application when the clinician application is online to the server.

In another aspect of the disclosed embodiment(s), a user application in a clinical trial operations system is provided, comprising: a user interface and network interface modules; user enrollment, user notification, user secure communication, user engagement, and user data capture service modules; and an offline portal proxy providing an offline portal service and data caches, allowing the user application to continue operating when offline from a server running a clinical trial operations service suite; and a synchronization capability, synchronizing information between the user application offline portal proxy and the clinical trial operations service suite when online with the server.

In yet another aspect of the disclosed embodiment(s), the above user application is described, further comprising: a health monitoring sensor adapted for sensing a patient's health, wherein the user application is a patient application running on a patient-located computer; the offline portal proxies a patient portal of the clinical trial operations service suite, the proxied patient portal comprising: a patient logon screen for a clinical trial; a patient enrollment menu for the clinical trial; an invitation option for at least one of another patient and clinician candidate to join the clinical trial; a messaging-oriented communication option to securely communicate with other clinical trial participants upon reestablishment of an online state; and health information specific goals of the clinical trial, wherein inputted information to the proxied patient portal is saved for online synchronization with the clinical trial operation service suite; and/or wherein: the user application is a clinician application running on a clinician-located computer; the offline portal proxies a clinician portal of the clinical trial operations service suite, the proxied clinician portal comprising: a clinician logon screen for a clinical trial; a clinician enrollment menu for the clinical trial; an invitation option for at least one of another patient and clinician candidate to join the clinical trial, and a tracking status of the invite; a messaging-oriented communication option to securely communicate with other clinical trial participants upon reestablishment of the online state; and health information specific goals of the clinical trial, wherein inputted information to the proxied clinician portal is saved for online synchronization with the clinical trial operation service suite; and/or further comprising, a display of at least one of a patient survey query, a schedule of patient events, and a patient-recorded record of observations; and/or wherein the online synchronization includes data from the health monitoring sensor; and/or further comprising, a display of at least one of a screen allowing a clinician to compose and send a notification, a clinician survey query, a schedule of clinician events, and a clinician-recorded record of observations; and/or further comprising, a health sensor operated by the clinician, wherein online synchronization includes data from the clinician's health sensor.

In yet another aspect of the disclosed embodiment(s), a method of operating a trial operations service suite in a clinical trial operations system is provided, comprising: running a trial operations service suite software on a computer; communicating with a user application running on a user device; displaying at least one of a service screen and user interface on the user device, the user interface querying for user input information for use in a clinical trial; receiving the user input on the user device; and synchronizing, when online with the computer, service suite information, service screen logic and user input information, collected by the user application when the user application was offline from the computer.

In yet another aspect of the disclosed embodiment(s), the above method is described, further comprising, when a data conflict arises during synchronization, wherein data changed in the user application while offline conflicts with data that has changed in the service suite since a previous synchronization, the service suite assumes the new data overrides the old data and continues synchronizing; and/or further comprising, the service suite notifying a coordinator to manually resolve the data conflict; and/or further comprising, resolving the conflict autonomously via an analytic module associated with the service suite; and/or wherein the user application is a patient application and the service suite provides a patient portal; and/or wherein the user application is a clinician application and the service suite provides a clinician portal.

In yet another aspect of the disclosed embodiment(s), a method of operating an application in a clinical trial operations system is provided, comprising: when the application is connected to a portal of a trial operations service suite, synchronizing portal and application data, service screens and logic, and data collected by the application while not connected; and when the application is not connected to the portal, using a proxy embedded in the application to continue providing service and collecting data according to a previously synchronized portal data, service screens, and service logic.

In yet another aspect of the disclosed embodiment(s), the above method is described, further comprising, when a data conflict arises during offline operation, wherein the application either requires portal data that is not available in a cache or depends on portal data that has changed while offline in such a manner as to be inconsistent with a cached service logic, the proxy stops supporting the service while offline; and/or further comprising, when a data conflict arises during offline operation, wherein the application either requires portal data that is not available in the cache or depends on portal data that has changed while offline in such a manner as to be inconsistent with the cached service logic, the proxy assumes the new data overrides the old data and continues supporting the service while offline; and/or wherein the application is a patient application and the portal is a patient portal; and/or wherein the application is a clinician application and the portal is a clinician portal.

The preceding Summary is intended to serve as a brief introduction to various features of some exemplary embodiments. Other embodiments may be implemented in other specific forms without departing from the scope of the disclosure.

DETAILED DESCRIPTION

The following detailed description describes currently contemplated modes of carrying out exemplary embodiments. The description is not to be taken in a limiting sense but is made merely for the purpose of illustrating the general principles of some embodiments. Therefore, based on the description, various modifications and changes may be made by one of ordinary skill in the art to devise alternative embodiments that perform or accomplish similar results, and such modifications and changes are understood to be within the spirit and scope of this disclosure.

Various features are described below that can each be used independently of one another or in combination with other features.

Introduction

The mobile-native clinical trial operations service suite disclosed in U.S. patent application Ser. No. 16/100,094 (referred to hereinafter as "the base patent application") provides a number of capabilities: such that the patients and their doctors who participate in a drug or device clinical trial benefit from automatic secure collection and storage of relevant data; such that each trial's investigators may securely receive appropriately anonymized (also referred to as de-identified) versions of that data, potentially in real time if allowed by the trial protocol, with automatic secure logging of data access, and may securely record corresponding research activities, observations, and conclusions in a fully traceable lab notebook tied to the trial, its data, and the data access logs; such that each trial's operational coordinators may design trial enrollment (including qualification and consent), engagement, data collection, and other information flow protocols quickly and easily within hours, and automatically create and deploy corresponding web and mobile device applications within minutes, without having to hire an engineering team to spend weeks or months translating the design into software; such that each trial's risk and compliance coordinators may analyze and extract traceability and accountability records as required; and such that all participants are able, if and as permitted by the trial protocol, to communicate with one another securely.

I. Hardware Architecture

Figure 1:
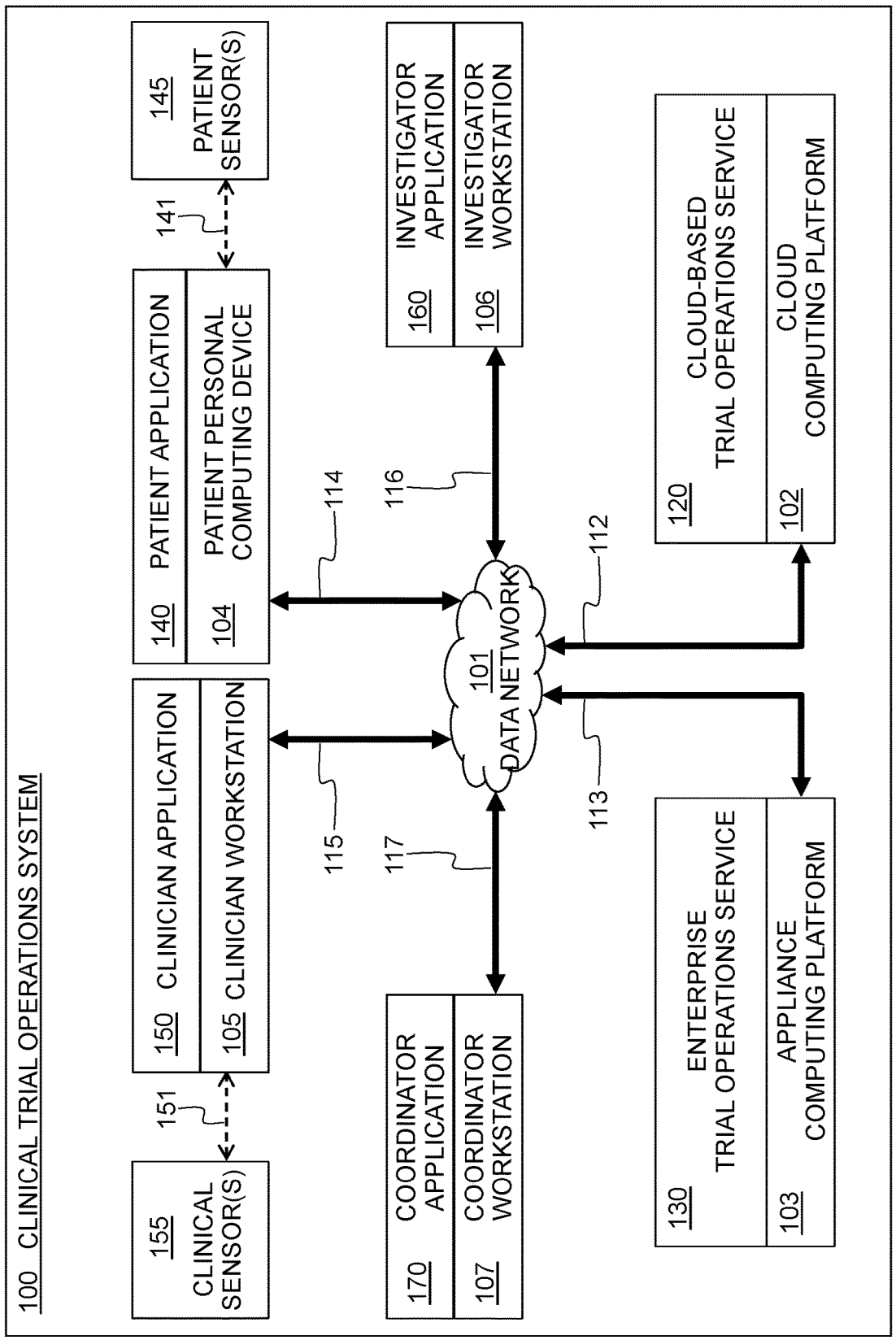
FIG. 1 illustrates an exemplary schematic block diagram of a clinical trial operations system.

FIG. 1 illustrates a schematic block diagram of a clinical trial operations system 100 according to an exemplary embodiment. FIG. 1 is a copy of FIG. 1 from the base patent application, and its description here is also copied therefrom to help provide an operational framework.

Data network 101 may interconnect the various elements of system 100. The network 101 may include one or more private networks as well as one or more public networks including the Internet. Constituent networks may include cellular mobile radio networks using various standards such as LTE; Wi-Fi networks serving public facilities such as airports, shopping centers, hospitals; Wi-Fi networks serving private facilities such as homes, labs, offices, and clinics; wired networks such as Ethernets within private facilities such as homes, labs, offices, and clinics; cable or DSL access networks; and any other form of data network.

Each category of participant may be considered to be a user of corresponding elements in system 100. A patient who participates in a clinical trial supported by system 100 may use a patient personal computing device 104, which may be a mobile device such as a tablet or smartphone, or a traditional computer such as a laptop or desktop, and which may connect to data network 101 via an interface 114 that may be implemented using any of numerous technologies as listed above or otherwise.

Patient application 140 may include software executed by the patient personal computing device 104 that may provide user interface (UI) and operational functions supporting the patient's interaction with system 100. Patient workstation 104 may also execute other software applications that fall outside system 100, in addition to, or in place of, patient application 140. For certain types of study, it may be necessary to incorporate health and environment information from sensors such as blood pressure monitors, heart rate monitors, personal fitness bands, smart watches, smart home products, and/or other similar devices.

For certain kinds of study, it may also be appropriate to incorporate health, event, and environment information from study-specific sensors provided to the patient, such as a custom drug dispenser that detects the time and conditions when a patient consumes a dose. Such devices are represented in the diagram by patient sensor(s) 145. In addition to study-specific sensors, such patient sensors may include biometric sensors (e.g., heart rate monitors, blood pressure sensors, blood sugar sensors, thermometers, etc.), environmental sensors (e.g., humidity sensors, temperature sensors, etc.), and/or event other event sensors. Furthermore, such sensors may include data received from a patient (e.g., indication of pain level or other appropriate factor, logging medication times and/or amounts, etc.).

Patient sensor(s) 145 may communicate with the patient personal computing device 104 via an interface 141 in order to provide sensor readings and related information. For each device represented by patient sensor(s) 145, interface 141 may include a wired connection such as a USB cable, and/or a wireless connection such as Bluetooth or Wi-Fi.

A doctor, advanced practitioner, or nurse who treats or oversees treatment of a patient participating in a clinical trial supported by system 100 may use a clinician workstation 105, which may be a mobile device such as a tablet or smartphone, or a traditional computer such as a laptop or desktop, and which may connect to data network 101 via an interface 115 that may be implemented using any of numerous technologies as listed above or otherwise.

Clinician application 150 may include software executed by clinician workstation 105 that provides UI and operational functions supporting the clinician's interaction with system 100. Clinician workstation 105 may also execute other software applications that fall outside system 100, in addition to, or in place of, clinician application 150.

For certain kinds of study, it may be necessary to incorporate health and environment information from sensors such as blood pressure monitors, heart rate monitors, thermometers, CT scanners, MRI scanners, and/or other diagnostic devices. Such devices are represented in the diagram by clinical sensor(s) 155. Clinical sensor(s) 155 may communicate with clinician workstation 105 via an interface 151 in order to provide sensor readings and related information. For each device represented by clinical sensor(s) 155, interface 151 may include a wired connection such as a USB cable or Ethernet network, a wireless connection such as Bluetooth or a Wi-Fi network, or a combination of such connections.

A technician, scientist, or other researcher who analyzes data and draws conclusions regarding the results of a clinical trial supported by system 100 may use an investigator workstation 106, which may be a mobile device such as a tablet or smartphone, or a traditional computer such as a laptop or desktop, and which may connect to data network 101 via an interface 116 that may be implemented using any of numerous technologies as listed above or otherwise.

Investigator application 160 may include software executed by investigator workstation 106 that provides UI and operational functions supporting the investigator's interaction with system 100. Investigator workstation 106 may also execute other software applications that fall outside system 100, in addition to, or in place of, investigator application 160.

A supervisor, designer, trial manager, site manager, risk manager, compliance manager, or other administrator who oversees one or more aspects of a clinical trial supported by system 100 may use a coordinator workstation 107, which may be a mobile device such as a tablet or smartphone, or a traditional computer such as a laptop or desktop, and which may connect to data network 101 via an interface 117 that may be implemented using any of numerous technologies as listed above or otherwise.

Coordinator application 170 may include software executed by coordinator workstation 107 that provides user interface and operational functions supporting the coordinator's interaction with system 100. Coordinator workstation 107 may also execute other software applications that fall outside system 100, in addition to or in place of coordinator application 170.

The system 100 may utilize a trial operations service that provides capabilities with which each participant may interact via the respective application. A distinct trial operations service may be used for each separate clinical trial in order to ensure strong data privacy protection, even when a single organization is operating multiple trials and therefore multiple trial operations services. Such an approach also prevents propagating any faults that may occur in one instance to other instances, thereby ensuring that no single fault compromises multiple trials.

The example of system 100 includes two kinds of trial operations service, but for any particular trial only one of those types is to be deployed, depending on the preference of the organization operating the trial.

A cloud-based trial operations service 120, which may include software functions executing in a cloud computing platform 102, may be selected by an organization that prefers to outsource its information technology operations to an expert in that field. For example, a biopharmaceutical research lab may prefer not to distract itself from its core competency, or a government research lab may require implementation using the services of a Federal Risk and Authorization Management Program (FedRamp)-approved provider.

An enterprise trial operations service 130, which may include software functions executing in an appliance computing platform 103, may be selected by an organization such as a large company with multiple capabilities that prefers to keep information technology operations in its own facility and network. For example, a medical device manufacturer may already have information technology competency due to the electronic and software-driven nature of its devices. Other reasons may also exist for choosing one or the other deployment option for the trial operations service.

One of ordinary skill in the art will recognize that system 100 may be implemented in various different ways without departing from the scope of the disclosure. For instance, the various elements of the system may be arranged in various different ways. As another example, various devices or elements may be implemented using multiple devices or sub-elements. Likewise, in some embodiments multiple devices or elements may be combined into a single device or element. In addition, various other elements may be included and/or various listed elements may be omitted in some embodiments.

II. Services

Many clinical trials take place in multiple locations, with separate personnel who may or may not interact with one another. In each of the participant categories described above, individual participants may be associated with one or more such locations, or sites, such that data access and communication permissions may be constrained to remain within each site. For example, a coordinator in the trial manager role may have permission to access data for all sites, while a coordinator in a site manager role may only have permission to access data for the assigned site. However, in clinical trial operations system 100 all sites associated with a particular clinical trial are supported by the same trial operations support service 120 or 130, thus ensuring commonality of trial data and procedures across all sites.

Figure 2:
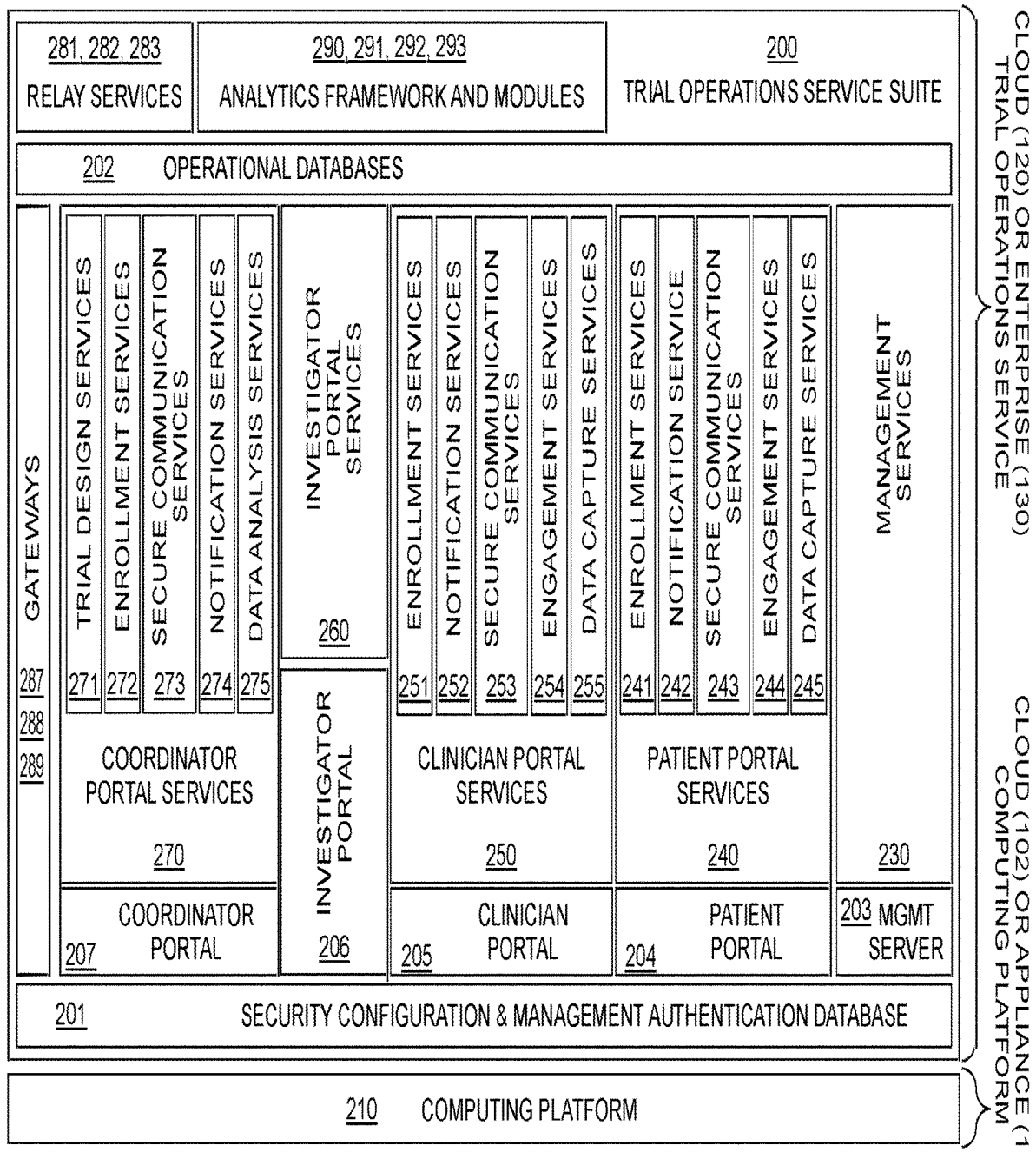
FIG. 2 illustrates an exemplary schematic block diagram of a trial operations service suite in a clinical trial operations system embodiment.

Enterprise trial operations service 130 and cloud-based trial operations service 120 may be similar, and both appliance computing platform 103 and cloud computing platform 102 provide similar capabilities. A unified view detailing these is provided in FIG. 2, which illustrates a schematic block diagram for a trial operations service suite 200 and computing platform 210 in a clinical trial operations system according to an exemplary embodiment. FIG. 2 is a composite of FIG. 2 and FIG. 3 from the base patent application, and much of its description here is repeated therefrom.

The mapping of trial operations service suite 200 modules to both cloud trial operations service 120 and enterprise trial operations service 130 is represented by the long upper bracket. The mapping of computing platform 210 modules to both cloud computing platform 102 and enterprise computing platform 103 is represented by the short lower bracket. Computing platform 210 is not further detailed here; it may be substantially as detailed in the base patent application.

Because clinical trial operations are subject to strict regulatory requirements regarding information security and privacy, computing platform 210 must be carefully selected and configured with features that accommodate those requirements. Encryption of data at rest and in motion, role-based data access permission capabilities, and bulletproof communication stacks are all important. A cloud computing platform 102 may be used only if it explicitly supports HIPAA compliance, which in addition to the features listed above also requires physical security and strong partitioning among customers so unrelated applications cannot interact with one another either intentionally or unintentionally. An organization choosing to deploy trial operations service suite 200 in an appliance computing platform 103 is obliged to satisfy these physical security and related requirements itself.

Security configuration and management authentication database 201 may provide a data repository specifically for information about the particular trial operations service suite 200 and its deployment in computing platform 210. Configuration data may include, but is not limited to, such persistent knowledge as how it relates to the network in which it resides, how the various function modules are deployed across potentially multiple physical and/or virtual computing machines, and licensed capacity. Security configuration data in particular may provide the mathematical basis of trust for establishing communication paths at the level of attaching the services hosted in trial operations service suite 200 to other services elsewhere in the network. Management authentication data may provide the credentials and permissions necessary to protect access to management functions.

Operational databases 202 may provide multiple data repositories specific to the clinical trial supported by trial operations service suite 200. This group of databases is architecturally distinct from security configuration and management authentication databases 201 for reasons of information privacy, data capacity differences, and transaction capacity differences. A detailed description of the specific data modules within operational databases 202 may be found in the base patent application.

Beyond that foundation, the functions of trial operations service suite 200 may fall into a few major groups. The first of these includes the management functions, which may provide ways to configure and control the trial operations service suite 200 and the underlying computing platform 210. Management server 203 may form the basis of the management function group, providing a network interface and an operating environment for the various management services. Management server 203 may include such components as a web server, a secure shell interface, a file transfer protocol server, and related capabilities typically used in the management of information technology systems. Management services 230 are not further detailed here; this element may be substantially as detailed in the base patent application.

The next major group of functions are the internal relay services 281, 282, and 283, and the external gateways 287, 288, and 289. Relay services provide capabilities for interaction among services of trial operations service suite 200. Gateways provide capabilities for communication and data access between trial operations service suite 200 and affiliated external systems, or among multiple related trial operations service suites 200. These functions may be substantially as detailed in the base patent application.

The next major group of functions is the data analytics framework 290 and its modules 2901, 292, and 293. These may provide an environment for automatic processes that analyze different types or multiple types of data as it comes into the system, looking for correlations indicating some important actionable fact. These functions may be substantially as detailed in the base patent application.

The final major group of functions in trial operations service suite 200 may provide access for various types of user in the trial community served by trial operations service suite 200. Each user category may be provided with a respective portal 204, 205, 206, or 207, which may include a web server dedicated to that category of users and which may support highly secure information presentation and interaction for multiple users within that category.

Multiple user roles may also be supported within each category, as well as site assignments for each user, depending on data access permissions encoded in a provisioning and authorization data subset of operational databases 202. For each user category, support for a variety of capabilities may be encapsulated within a corresponding set of services 240, 250, 260, or 270 built atop the corresponding portal

204, 205, 206, or 207, partitioned from the others to prevent inappropriate information crossover, and interacting with the corresponding application 140, 150, 160, or 170 of system 100. Each user category's portal and services are described below.

Patient portal 204 and patient portal services 240 may provide access for patients participating in the supported clinical trial, interacting with patient application 140. The patient user category may include user accounts not only for a particular patient participating in a clinical trial, but also any of that patient's family members or representatives such as a formally declared HIPAA agent or a holder of healthcare power of attorney who the patient has designated to have access to the system. Each patient account may have specific permissions to view data, update data, create diary and journal entries, receive notifications, and the like, depending on the corresponding records in a provisioning and authorization data subset of operational databases 202 as established by the patient, or the trial protocol as established by a coordinator. Patient portal 204 may provide, through patient application 140, a base view whereby the patient user can see account status, see overviews of each available service such as whether unviewed notifications exist, and select an available service to activate.

Patient portal services 240 may include any or all of the services shown depending on the requirements of the particular clinical trial being supported by trial operations service suite 200. Additional services not shown or described may also be created within this service framework.

Patient portal services 240 may include a group of enrollment services 241, a notification service 242, a group of secure communication services 243, a group of engagement services 244, and a group of data capture services 245. Each of these services may be substantially as detailed in the base patent application, except for enhancements to eligible procedures in support of offline operation by patient application 140, as provided in the present embodiment(s) and described, for example, in the context of FIG. 6, FIG. 7, and FIG. 8.

Clinician portal 205 and clinician portal services 250 may provide access for clinicians with one or more patients participating in the supported clinical trial, interacting with clinician application 150. The clinician user category may include user accounts not only for a doctor treating a particular patient participating in a clinical trial, but also any of that doctor's staff, partners, associated advanced practitioners, or nurses who also participate in treatment or care of a participating patient. Each clinician account may have specific permissions to view data, update data, create diary entries, receive notifications, and the like, depending on the corresponding records in provisioning and authorization data subset of operational databases 202 as established by the primary clinician, or the trial protocol as established by a coordinator.

Clinician portal 205 may provide, through clinician application 150, a base view whereby the clinician user can see account status, see overviews of each available clinician-specific service such as whether unviewed notifications exist and select an available service to activate, view a list of associated patients participating in the supported clinical trial and corresponding overviews of patient-related services, and select a patient and service from that list.

Clinician portal services 250 may include any or all of the services shown depending on the requirements of the particular clinical trial being supported by trial operations service suite 200; additional services not shown or described may also be created within this service framework.

Clinician portal services 250 may include a group of enrollment services 251, a group of notification services 252, a group of secure communication services 253, a group of engagement services 254, and a group of data capture services 255. Each of these services may be substantially as detailed in the base patent application, except for enhancements to eligible procedures in support of offline operation by clinician application 150, as provided in the present embodiment(s) and described for example, in the context of FIG. 6, FIG. 7, and FIG. 9.

Investigator portal 206 and investigator portal services 260 may provide access for investigators handling the research and analysis responsibilities in the supported clinical trial, interacting with investigator application 160, and may be substantially as detailed in the base patent application.

Coordinator portal 207 and coordinator portal services 270 may provide access for people in charge of managing various aspects of the trial, interacting with coordinator application 170. The coordinator user category may include user accounts for various individuals with distinct or overlapping responsibilities, including but not limited to trial design, everyday trial operations, and compliance. Each coordinator account may have specific permissions to view data, update data, change the trial design, send notifications, and the like, depending on the corresponding records in a provisioning and authorization data subset of operational databases 202 as established by the primary coordinator. Coordinator portal 207 may provide, through coordinator application 170, a base view whereby the coordinator user can see account status, see overviews of each available coordinator-specific service, and select an available service to activate.

Coordinator portal services 270 may include any or all of the services shown depending on the requirements of the particular clinical trial being supported by trial operations service suite 200; additional services not shown or described may also be created within this service framework.

Coordinator portal services 270 may include a group of enrollment services 272, a group of secure communication services 273, a group of notification services 274, and a group of data analysis services 275, all of which may be substantially as detailed in the base patent application.

Coordinator portal services 270 may also include a group of trial design services 271, which may support configuration of trial operations service suite 200 for the particular clinical trial being supported. Trial design services 271 may be used both at the beginning of a trial to set its initial design, and during the trial to change aspects of its design that may need adjustment as the trial progresses. Trial design services 271 may provide selections to configure whether specific services are available in each group of portal services 240, 250, and 260, such as which communication modes may be activated, as well as other configuration items such as whether gateways 287, 288, and 289 are active and if so with what other systems they may interoperate, what kind of inter-user communication, notification, and invitation pairings are permitted, and what kind of data analytics are activated.

Trial design services 271 may also provide capabilities for designing detailed user interaction procedures such as screen layouts, order of presentation and text for participant qualification and informed consent protocols, supported sensors both mandatory and optional, sensor data collection schedules, branding imagery and wording, wording of internal and external notification templates, wording of invitation templates, structure of surveys and status queries, structure and emphasis of diary or journal entry templates, structure and emphasis of lab notebook entry templates, supported data access query templates, data access result display formats, and every other aspect of user interaction supported by applications 140, 150, and 160. Trial design services 271 may even alter the look and capabilities of coordinator application 170 itself.

Trial design services 271 may also provide capabilities for indicating whether a particular application element or service, such as those mentioned above, may or may not be utilized while the application is offline. That is, even when a particular service can technically continue to operate during a break in the connection between application and service, as detailed in the methods section below, a coordinator user may elect to disable this capability explicitly. This may be appropriate, for example, if a regulatory authority does not permit offline operation for a particular category of data such as patient consent.

In an exemplary embodiment, trial design services 271 may be implemented by embedding in trial operations service suite 200 an enhanced version of the application factory system disclosed in U.S. Pat. No. 8,719,776, which is incorporated herein by reference. Enhancements in this regard may be substantially as detailed in the base patent application.

Figure 3:
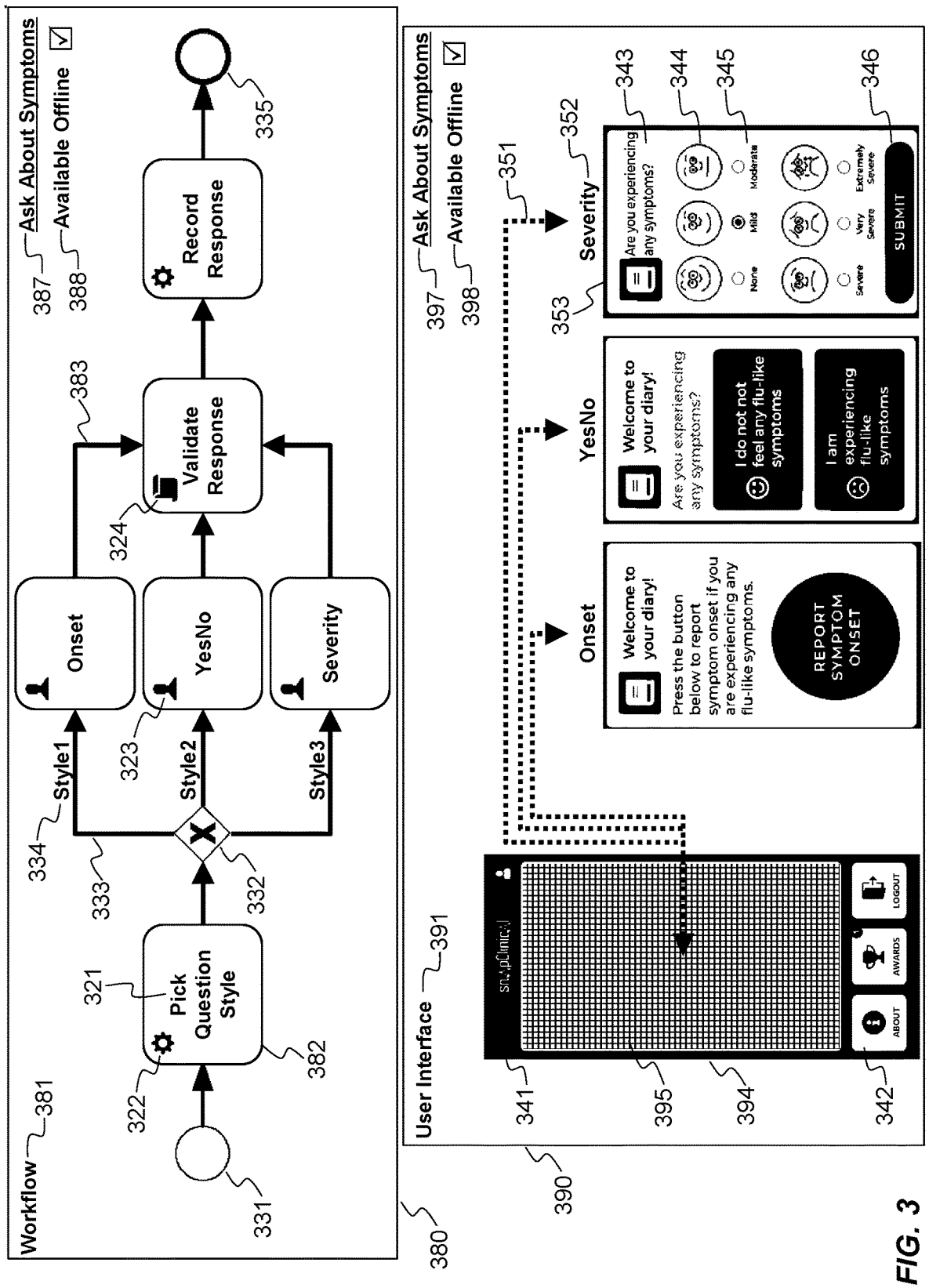
FIG. 3 illustrates an exemplary workflow and corresponding user interface screens which may be included in a web or mobile device application in a clinical trial operations system embodiment.

FIG. 3 illustrates an exemplary workflow and corresponding exemplary user interface screens which may be included in a patient application 140. Example workflow 380 may be created using the application factory system embedded in trial design services 271, and customized to a specific clinical trial according to the dictates of its protocol using the Flowable-based workflow palette in conjunction with the composition studio's visual programming toolkit. Similarly, example user interface screens 390 may be created using the application factory system embedded in trial design services 271, and customized to a specific clinical trial according to the dictates of its protocol using the various palettes available in the composition studio's design toolkit. Note that the exact nature of the workflow shown in FIG. 3 is a simple patient questionnaire, which is visibly related by the nature of its depicted imagery and text to the clinical trial field of use pertinent in the present embodiment(s). However, it is described here in terms of its logical and structural symbology in order to focus on the capability of building relevant workflows rather than on any specific workflow topic. A coordinator user of trial design services 271 may create any number of such workflows and user interfaces to represent the trial protocol, which may then in turn be assembled into patient, clinician, investigator, or coordinator applications 140, 150, 160, or 170 respectively.

The representation of example workflow 380 and its example user interface 390 thus includes a number of symbols with specific meanings in the context of trial design services 271. Workflow label 381 and user interface label 391 distinguish between the logical and graphical specifications, while workflow name 387 and user interface name 397 contain text strings created by the designing coordinator user to distinguish this workflow and its user interface from others. The same value, "Ask About Symptoms" in the example, is shown for both names 387 and 397 to indicate that this workflow 380 and this user interface 390 are related to one another.

Figure 4:
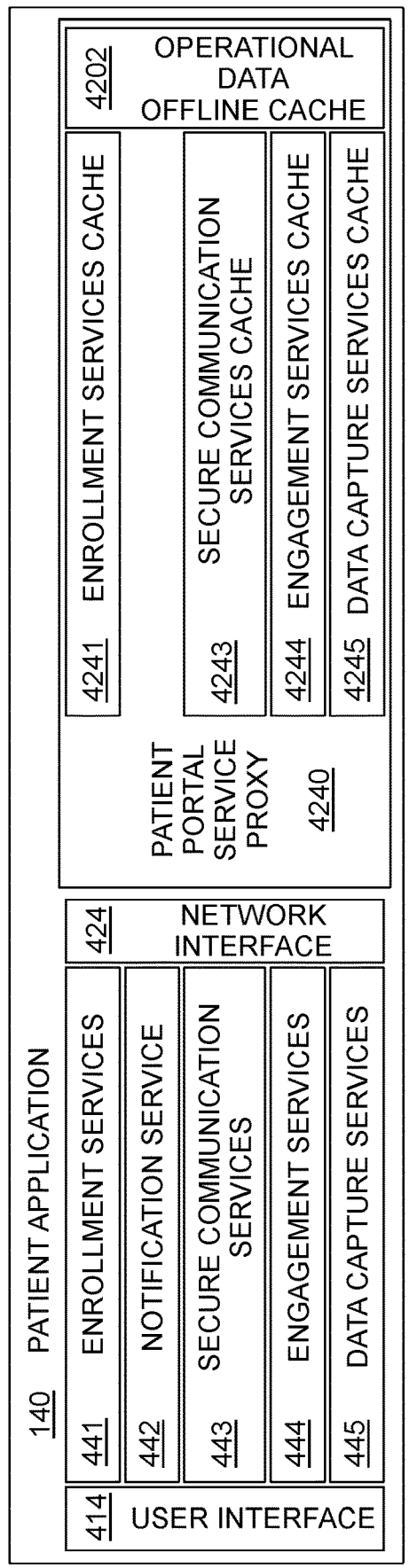
FIG. 4 illustrates an exemplary schematic block diagram of a web or mobile device application in a clinical trial operations system according to an exemplary embodiment of the offline mode aspect.
Figure 4:
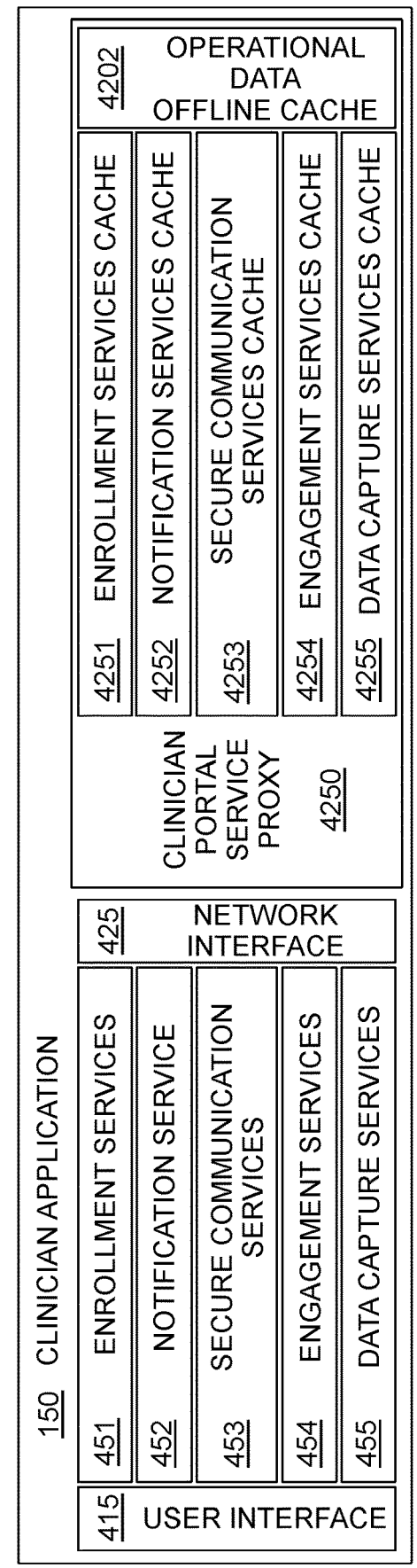

Of particular relevance to the present disclosure are workflow attribute 388 and user interface attribute 398, which both indicate that the elements of this workflow 380 and this user interface 390 are available offline. That is, their structure and content may be pushed to application 140 or 150 for use even when there is no connection to the corresponding portal services 240 or 250. Refer to FIG. 4 and later for additional details on this capability.

The flow aspect of example workflow 380 begins at start symbol 331 and is complete at end symbol 335. Other symbols not shown may represent waiting for a message from an external entity or suspending for a period of time. To get from start to end, a variety of actions, decisions, and transitions may occur. Each action block 382 provides an opportunity for the application implementing example workflow 380 to do something useful, which typically may be summarized using the action block name 321. The actual details of what the action block 382 does may be specified by invoking a composition studio canvas and palette that corresponds to the action block type. The action block name 321 may also match a named element in the corresponding canvas, so as to specify a definitive relationship between the workflow action block and the underlying action. Each transition 383 may provide a time-ordered flow from a start symbol 331 or action block 382 to another action block 382, an end symbol 335, or a decision block 332. Each decision block 332, of which only one is present in FIG. 3, may provide a branch in the flow based on a data item identified by the preceding action block 382. Each possible value of the data item may then be used as a transition name 334 associated with a corresponding named transition 333, such that the decision block 332 directs the flow along the corresponding path according to the selected value. Note that the only type of decision block 332 shown in FIG. 3 is similar in meaning to a CASE statement in a traditional computer programming language. Other decision block types may be used, each one represented using a different symbol not shown, including such common operations as logical and numerical comparisons, as well as a multipath operation that splits the flow into two or more simultaneous sequences.

Three types of action block are depicted here using distinct icons to represent each, and others may be inferred from the composition studio descriptions in the base patent application and in U.S. Pat. No. 8,719,776, which together describe more than this number of canvas/palette combinations. Action block type 322 may manipulate data, such as reading a variable in the type 322 action block 382 labeled "Pick Question Style" or writing a variable in the type 322 action block 382 labeled "Record Response." Within the composition studio of trial design services 271, selecting or creating an action block 382 of type 322 may invoke the data palette of the data and logic canvas in order to specify the pertinent data items and what is to be done with them. This palette and canvas are not further described here; refer to the aforementioned antecedents for details.

Action block type 323 may cause the presentation of a corresponding screen or subscreen according to the relationship indicated via the action block name 321. Within the composition studio of trial design services 271, selecting or creating an action block 382 of type 323 may invoke the user interface canvas to specify the corresponding user interface elements. More detail regarding the construction of corresponding screens follows in the context of example user interface 390.

Action block type 324 may cause the execution of an algorithm, effectively a subroutine that matches Decision action block name 321. Within the composition studio of trial design services 271, selecting or creating an action block 382 of type 324 may invoke the logic palette of the data and logic canvas in order to specify the algorithm to be executed. Any operation that may be expressed in the data and logic canvas may be incorporated in the corresponding algorithm; thus an action block 382 of type 324 may perform calculations, interact with other entities through external communication, start or stop sensors or actuators in the mobile device running application 140 or 150, or any other operation available in that portion of the composition studio. This palette and canvas are not further described here; the aforementioned antecedents provide details.

As previously noted, example user interface 390 is associated with example workflow 380 through the common value in their respective names 387 and 397. In the user interface canvas, a coordinator user may arrange passive graphical elements such as text 343 and icons 344, and active graphical elements such as selectors 345 and buttons 346. These arrangements may be grouped into fixed areas such as header 341 and footer 342 so that they appear in every variation of screen 394, or they may be grouped into subscreens 353 linked to a variable area 395 by subscreen relationships 351 so that the appropriate visual and control arrangement may be selected according to workflow logic. Subscreen names 352 would then be used to associate each subscreen 353 with an action block of type 323 by matching its action block name 321.

One skilled in the art will appreciate that the fixed areas header 341 and footer 342 in screen 394 may have as easily been designed using additional variable areas 395 and accompanied by additional subscreens 353 with corresponding name relationships 352 to additional action blocks 382 of type 323. Further, the specific decisions regarding structure and design of a workflow and its user interface are entirely at the coordinator user's discretion and may take any conceivable form, including more or fewer elements in different orders with simpler or more complex logic. Similarly, the values of names 387, 397, 321, 334, and 352, as well as the content and form of graphical elements such as text fields 343, images 344, and buttons 345 and 346, are also design choices that may be exercised by the coordinator user. One skilled in the art will also appreciate that the range of logic and graphic elements is not limited to those described here. The full set of capabilities supported by the application factory system embedded in trial design services 271 may be utilized in designing real workflows and user interfaces for a specific clinical trial. Further, it should be noted that the specific graphic style of each symbol depicted in FIG. 3 is important only to the extent that it evokes the workflow or user interface element it is meant to represent. Other symbols and symbol positions may be used equally as well within the scope of the present embodiment(s).

FIG. 4 provides detail of patient application 140 and clinician application 150. In general, each of the mobile/web applications in the base patent application may be designed as a reflection of the services in the corresponding portal. Thus patient and clinician applications 140 and 150 may incorporate client-side implementations of these services, represented in the figure as enrollment, notification, secure communication, engagement, and data capture services, respectively 441, 442, 443, 444, and 445 for the patient and 451, 452, 453, 454, and 455 for the clinician. Application behaviors with respect to each of these services remain as described previously in the base patent application. Patient and clinician applications 140 and 150 may also include network interfaces 424 and 425 respectively, which facilitate interaction with the corresponding portal—204 and 205 respectively—and its services—240 and 250 respectively—via data network 101. Further, patient and clinician applications 140 and 150 may include user interfaces 414 and 415 respectively, which facilitate actual user interactions and specialize the presentation of each service to the corresponding user type.

In the various embodiments, patient and clinician applications 140 and 150 are enhanced to include functionality that facilitates offline use. That is, each application may continue to provide some services even when its network interface 424 or 425 cannot communicate with the corresponding portal 204 or 205. Patient portal service proxy 4240 embodies this offline capability in patient application 140, while clinician portal service proxy 4250 does so in clinician application 150. Each portal service proxy stands in for the portal to execute in the application the portal-side functionality of any services that can be accessed while offline. Logic and data associated with each service, including in particular workflows and associated user interface screens that—like those in example workflow 380 and example user interface 390—have been identified as Available Offline, are provided to the application whenever it interacts with the portal.

For each service, the portal-side logic (workflows and screens) is stored in the corresponding service cache for execution as needed by portal service proxy 4240 or 4250. That is, enrollment services cache 4241 may embody in patient application 140 the logic of enrollment services 241 in patient portal services 240, allowing patient portal service proxy 4240 to take the latter's place when offline. Similarly, secure communication services cache 4243 may stand in for secure communication services 243, engagement services cache 4244 may stand in for engagement services 244, and data capture services cache 4245 may stand in for data capture services 245. The same principles apply in clinician application 150, where enrollment services cache 4251 may embody the logic of enrollment services 251 in clinician portal services 250, allowing clinician portal service proxy 4250 to take the latter's place when offline, notification services cache 4252 may stand in for notification services 252, secure communication services cache 4253 may stand in for secure communication services 253, engagement services cache 4254 may stand in for engagement services 254, and data capture services cache 4255 may stand in for data capture services 255.

Portal-side data may be baselined while online and stored in operational data offline cache 4202, which may stand in for the user-specific and service-specific portions of operational databases 202. When a proxy 4240 or 4250 executes a service offline from one of its services caches, data that is generated or changed as a result may in turn be stored in operational data offline cache 4202. These new or changed data may be synchronized with operational databases 202 upon returning to online mode.

While the examples shown may illustrate many individual modules as separate elements, one of ordinary skill in the art would recognize that these modules may be combined into a single functional block or element. One of ordinary skill in the art would also recognize that a single module may be divided into multiple modules.

III. Methods of Operation

Fundamentally, any service or service procedure that either manipulates or originates user data independent of any other user may be operated offline using this construct. However, any service that depends on live interaction with other users or their data cannot be proxied locally and therefore cannot operate offline. Patient and clinician users, along with their corresponding applications, may operate offline as described in the following procedures. Investigator and coordinator users, along with their corresponding applications, are not provided the ability to operate offline due to their roles as handlers of large data sets and system settings, respectively; in both cases caching of data in the application would be counterproductive. FIG. 5-FIG. 10C detail the offline support aspect of the various embodiments described herein.

Figure 5:
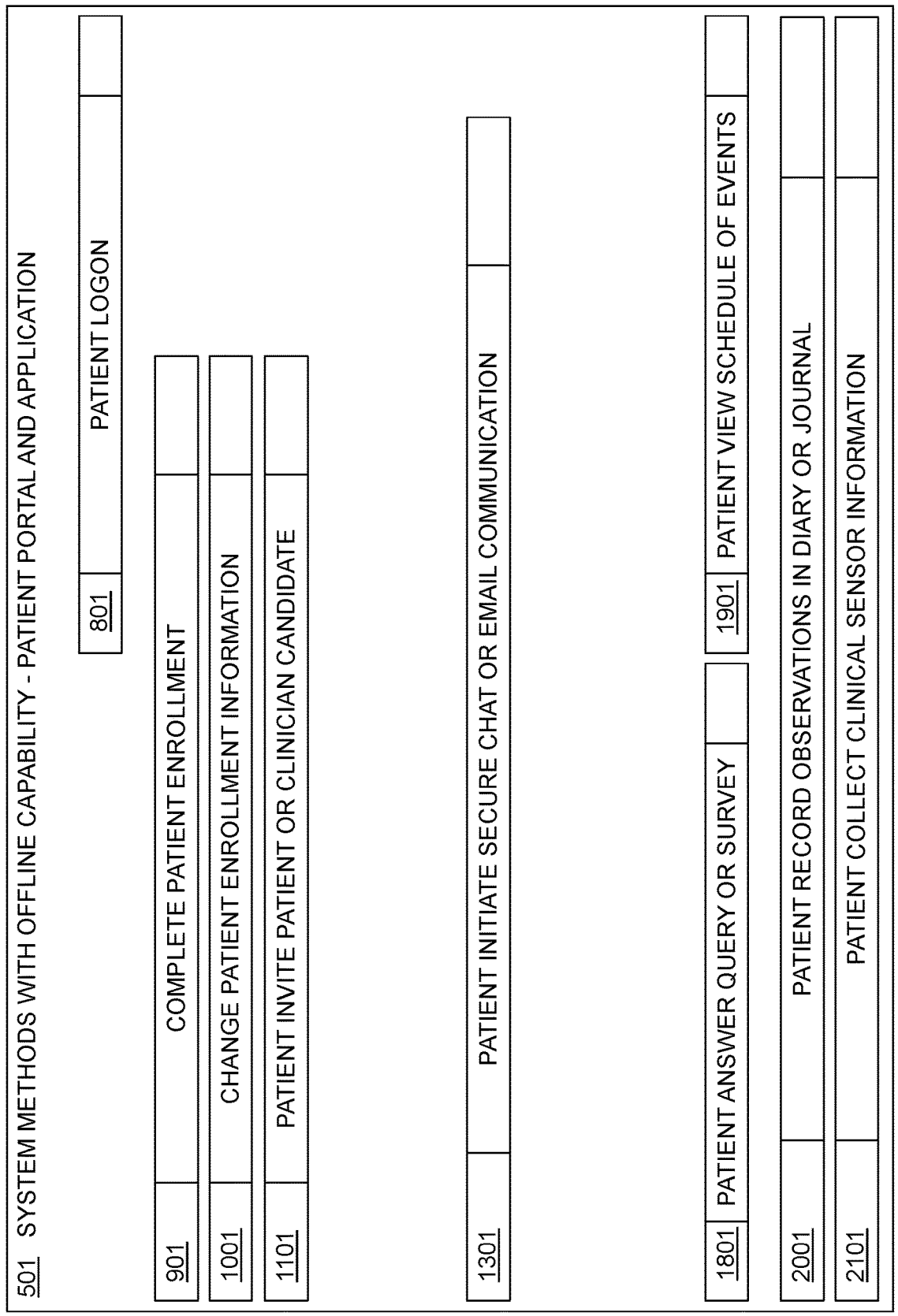
FIG. 5-FIG. 10C illustrate a group of exemplary processes distributed among a patient or clinician application, patient or clinician portal, and other elements of a trial operations service suite in a clinical trial operations system according to an embodiment(s) of the offline mode aspect.

FIG. 5 illustrates a group of processes distributed among a patient application, patient portal, and other elements of a trial operations service suite in a clinical trial operations system according to an exemplary embodiment. In particular, the processes shown in the figure are those which may be supported in the offline mode. Each process from FIG. 5 of the base patent application that may be supported in offline mode is shown here with its reference number incremented by one. Processes from FIG. 5 of the base patent application that are not shown here require live interactions with the service or with other users, making them unsuitable for offline operation. The processes supporting offline operation may include logon, enrollment completion, personal data update, participant invitations, secure message sending, survey completion, calendar utilization, diary and journal entries, and sensor data collection. The processes not suitable for offline operation may include self-registration, notification receipt, receipt of secure messages, and secure communication involving audio/video calls. Note that each of these processes may be a considered a category comprising workflows and associated user interfaces built up and specialized to a particular clinical trial using trial design services 271. That is, each process generalizes a class of workflows supporting a corresponding type of information and user interaction pertinent in the clinical trial context.

Figure 6:
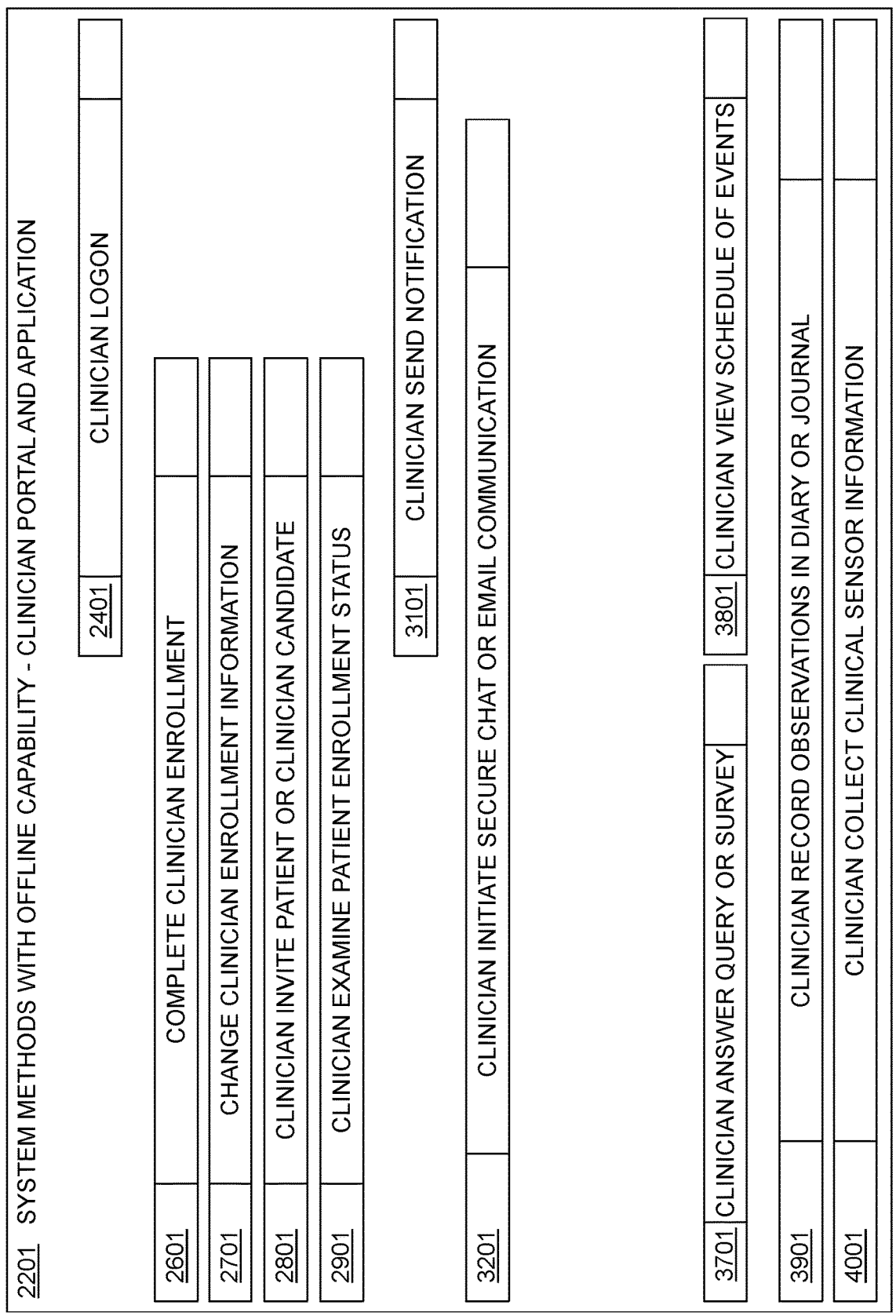

FIG. 6 illustrates a group of processes distributed among a clinician application, clinician portal, and other elements of a trial operations service suite in a clinical trial operations system according to an exemplary embodiment. In particular, the processes shown in the figure are those which may be supported in the offline mode. Each process from FIG. 22 of the base patent application that may be supported in offline mode is shown here with its reference number incremented by one. Processes from FIG. 22 of the base patent application that are not shown here require live interactions with the service or with other users, making them unsuitable for offline operation. For example, clinician logon process 2400 in the base patent application is shown here as "offline" clinician logon process 2401, and so forth for the remaining processes and/or modules shown in FIG. 6. As process or module or step, 2201, 2601, 2701, 2801, 2901, 3101, 3201, 3701, and 3801, 3901, and 4001 are "offline" versions of their counterpart in the base patent application, their explanation is understood to be self-evident. The processes supporting offline operation may include logon, enrollment completion, personal data update, participant invitations, patient enrollment status monitoring, notification sending, secure message sending, survey completion, calendar utilization, diary and journal entries, and sensor data collection. The processes not suitable for offline operation may include self-registration, notification receipt, receipt of secure messages, and secure communication involving audio/video calls. Note that each of these processes may be a considered a category comprising workflows and associated user interfaces built up and specialized to a particular clinical trial using trial design services 271. That is, each process generalizes a class of workflows supporting a corresponding type of information and user interaction pertinent in the clinical trial context.

FIG. 7-FIG. 10C illustrate additional detail for the offline aspects of the processes in FIG. 5 and FIG. 6.

Figure 7:
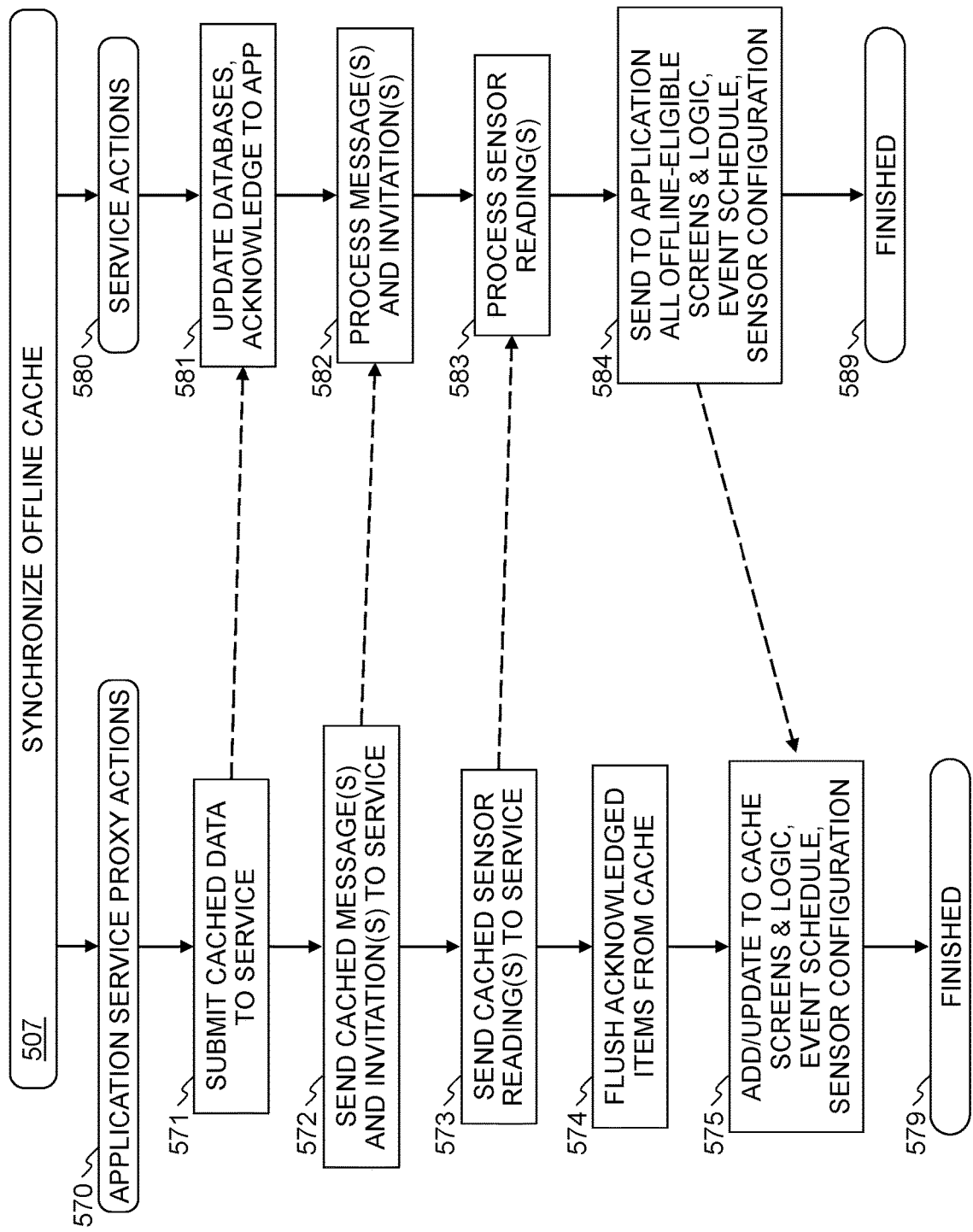

FIG. 7 depicts a method of synchronizing a portal service proxy 4240 or 4250 with its corresponding portal services 240 or 250, respectively. This procedure may be invoked at any time by one of the offline-capable procedures listed in FIG. 5 and FIG. 6. Synchronization services may involve sending from the proxy to the portal any updated or newly created data items stored in an operational data offline cache 4202 for storage in operational databases 202, as well as receiving in the proxy a set of fresh workflow logic and user interface screen formats from the portal. This synchronize offline cache procedure 507 involves two actors, an application's portal service proxy 4240 or 4250 represented in the figure by application service proxy actions sub-process 570, and a portal services framework 240 or 250 represented in the figure by service actions sub-process 580. As in the base patent application, solid arrows represent temporal ordering and information flow within a sub-process, and dashed arrows represent temporal ordering and information flow between sub-processes.

Procedure 507 begins at operation 571, in which the proxy may submit cached data to the service. Cached data here refers to any information created or modified by a user in the process of executing a service while offline. This data is sent to the service, which at operation 581 may update operational databases 202 as if they had been submitted in the normal course of executing the corresponding procedures described in the base patent application. The service also may acknowledge the success or failure of this operation back to the application, and continue as shown if the various data updates were successful. The failure case is not depicted; in that situation the procedure would terminate and be retried at a later opportunity.

At operation 572, the proxy may send cached messages and invitations to the service. Cached messages refers here to any chat or email messages created by the user while offline, through the corresponding secure communication services 243 or 253 interacting with proxy 4240 or 4250 executing logic in secure communication services cache 4243 or 4253 respectively. Cached invitations refers here to any invitations created by the user while offline, through the corresponding enrollment services 241 or 251 interacting with proxy 4240 or 4250 executing logic in enrollment services cache 4241 or 4251 respectively. Upon receiving these, the service at operation 582 may process these new messages and invitations as if they had been received in the normal course of executing the corresponding procedures described in the base patent application.

At operation 573, the proxy may send cached sensor readings to the service. Cached sensor readings refers here to any sensor readings stored in operational data offline cache 4202 by proxy 4240 or 4250 according to logic in data capture services cache 4245 or 4255, respectively. Upon receiving these, the service at operation 583 may process these new readings as if they had been received in the normal course of executing the corresponding procedures described in the base patent application.

Upon sending all cached items to the service, the proxy may at operation 574 flush acknowledged items from the cache so they are not sent again. This may take the form of deleting transaction logs recorded by operational data offline cache 4202 at each of its updates, deleting the actual data items from cache 4202 if they are no longer needed for future offline operation, or any other similar technique as commonly used in database synchronization approaches.

Having processed all the received offline data, messages, invitations, and sensor readings, at operation 584 the service may send to the proxy updated versions of the various items that may be cached to support future offline operation, which may have changed at the portal either during the previous offline period or as a result of processing the received offline information. Items to provide for caching may include updated screens and logic for all services that are eligible for execution while offline, scheduled events (for patient, clinician, etc.) that may have changed or been created while previously offline, and sensor configuration updates. Not mentioned in the figure but also sent if necessary are messages for the user that were received while previously offline, and user-specific data items from operational databases 202 that may be needed by the offline logic and screens. Upon receiving these items at operation 575, the proxy in turn may add them to or update them in its various services caches and offline data cache.

At this point, both actors' procedural threads come to a close at operations 579 and 589 respectively.

Note that the exact order of operation shown in FIG. 7 is exemplary and used primarily for convenience in the description; other orders are possible and may be more efficient in an implementation. The different types of data being synchronized may be transferred in groups in the order shown, transferred in groups in some other order, or transferred individually according to the order in which they were actually changed/created at the application's portal service proxy 4240 or 4250. The last approach effectively interleaves the various data types by time, and may be the simplest to implement.

Note also that in certain circumstances the data submitted for synchronization may conflict with the current state of operational databases 202. This might happen, for example, when the update represents answers to a survey that changed while the application was offline, a message to a user who is no longer registered, sensor readings for a sensor that is no longer being monitored or for which the monitoring rate has been reduced. Any update in which the data was determined in part or affected by cached data or logic originally provided by the service and changed at the service since the time of its caching at the application may produce such a conflict. When this happens the service may ignore the update, or it may record the update as a separate entry and note the conflict, depending on whether the new data is simply out of date or represents a more complex situation. If it's a true conflict, the service may also create a notification to a coordinator with appropriate privileges who may resolve the conflict manually, or an analytic module may notice the conflict and act to resolve it autonomously.

Figure 8:
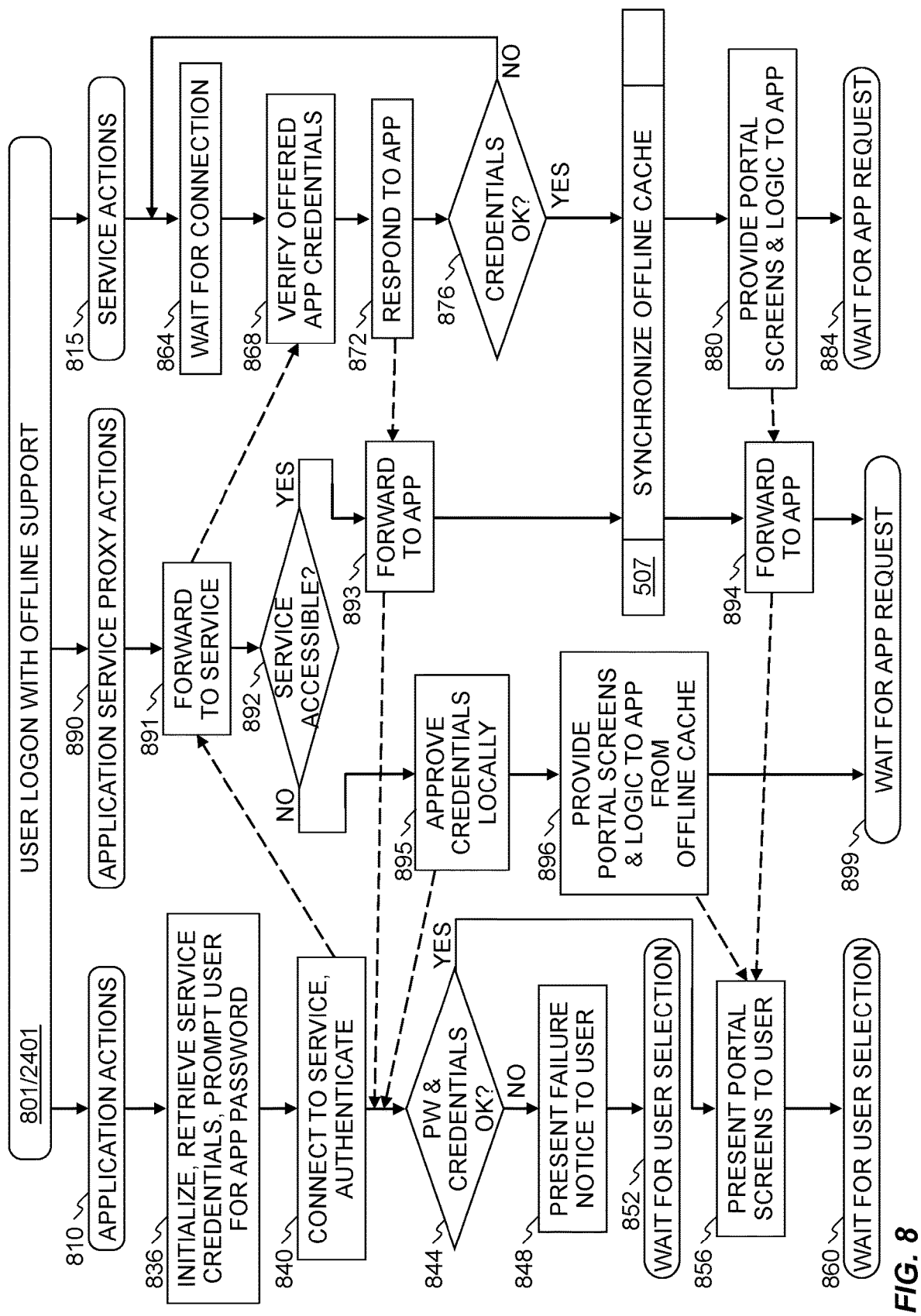

FIG. 8 depicts a user logon process enhanced with offline support. This process may be used by either a patient or a clinician, updating both patient logon process 800 and clinician logon process 2400 from the base patent application to become both patient logon process 801 and clinician logon process 2401 as shown in FIG. 5 and FIG. 6 respectively. Due to this dual role, the process is labeled user logon with offline support process 801/2401. As in the base patent application, process 801/2401 is a prerequisite for as well as an embedded operation in every other patient and clinician process that is enhanced to provide offline operation, which will be shown in FIG. 9.

Four primary actors participate in this process: a user, which may be either a patient or a clinician; an application, which may accordingly be the patient application 140 device app or the clinician application 150 web app; an application service proxy, which may accordingly be either patient portal service proxy 4240 or clinician portal service proxy 4250; and a service, which is the various elements of trial operations service suite 200, including in particular patient portal 204 or clinician portal 205 respectively. In the figure, the operations performed by three of these actors are shown as part of interacting sub-processes: application actions 810, application service proxy actions 890, and service actions 815. The user is not represented in this figure due to space considerations, but the corresponding actions and interactions with application actions 810 may be identical to those of either the user actions 805 sub-process in FIG. 8 of the base patent application or the user actions 2405 sub-process in FIG. 24 of the base patent application, except with respect to the "first logon" operations in the latter since those can't be accomplished while offline. As in the base patent application, solid arrows in the figure represent temporal ordering and information flow within a sub-process, and dashed arrows represent temporal ordering and information flow between sub-processes.

User logon with offline support process 801/2401 begins at operation 820/2420 (not shown), in which the user may activate the application. At operation 836, the application may initialize and retrieve its service credentials and app password from protected storage, prompt the user to enter the app password, then use the service credentials at operation 840 to connect and authenticate with patient portal 204 or clinician portal 205 as appropriate. In order to facilitate offline operation, this connection attempt may be mediated through patient portal service proxy 4240 or clinician portal service proxy 4250 as appropriate. Thus at operation 891 the service proxy may forward the connection attempt to the corresponding portal and use the success or failure of that forwarding action to determine at operation 892 whether the service is accessible or not. The service proxy may also save the result of its decision for future use.

In parallel, the user at operation 824 (not shown) may enter the app password. In the meantime, the portal has been waiting for this connection, represented as operation 864. Upon arrival of the connection attempt, the portal may at operation 868 verify the offered app credentials and respond accordingly at operation 872. In this case, the application is online and the service proxy at operation 893 forwards the response to the application. If the credentials were not accepted, the decision at operation 876 causes server sub-process 815 to return to operation 864 and await another connection attempt. If the connection attempt doesn't arrive at the portal due to the application being offline, the service proxy at operation 895 may approve the credentials locally; there is no path for the credentials not being accepted in this case, because both the application and the service proxy are local so they will always match. Either way, application sub-process 810 may check at operation 844 whether the response indicated acceptance of the credentials, as well as whether the user entered the correct app password. If either is not accepted, the application may present a failure notice to the user at operation 848 and wait for a user selection at operation 852. If the credentials and password were both accepted and the application is offline as determined by the service proxy at operation 892, the service proxy at operation 896 may provide the portal screens and logic to the application based on the contents of the proxy's services and data caches. If the application is online, the application service proxy and the service may exchange data and logic using synchronize offline cache procedure 507, previously described. Then the portal may provide the application with screens and logic associated with portal services at operation 880, and the application service proxy forwards same to the application at operation 894. Whether the portal screens and logic come from the service proxy while offline or the service itself while online, the application may in turn present the initial screen of that view to the user at operation 856. The user then may view the presented screen, whether the failure notice of operation 848 or the portal view of operation 856, at operation 828/2515 (not shown).

At this point, user logon with offline support process 801/2401 is complete, with each sub-process quiescing in its own way. User sub-process 805/2405 (not shown) simply finishes at operation 832/2520 (not shown), with nothing further for the user to do. In application sub-process 810, the application remains running, so its quiescent state is waiting for the user's next selection at operation 860. Similarly, patient portal 204 or clinician portal 205 if online, or patient portal service proxy 4240 or clinician portal service proxy 4250 if offline, has an established session for this user, with the application connected and authenticated, so it too quiesces in an active state waiting for the next application request at operation 884 if online or operation 899 if offline. Any of the other user methods may be selected in this state.

Figure 9:
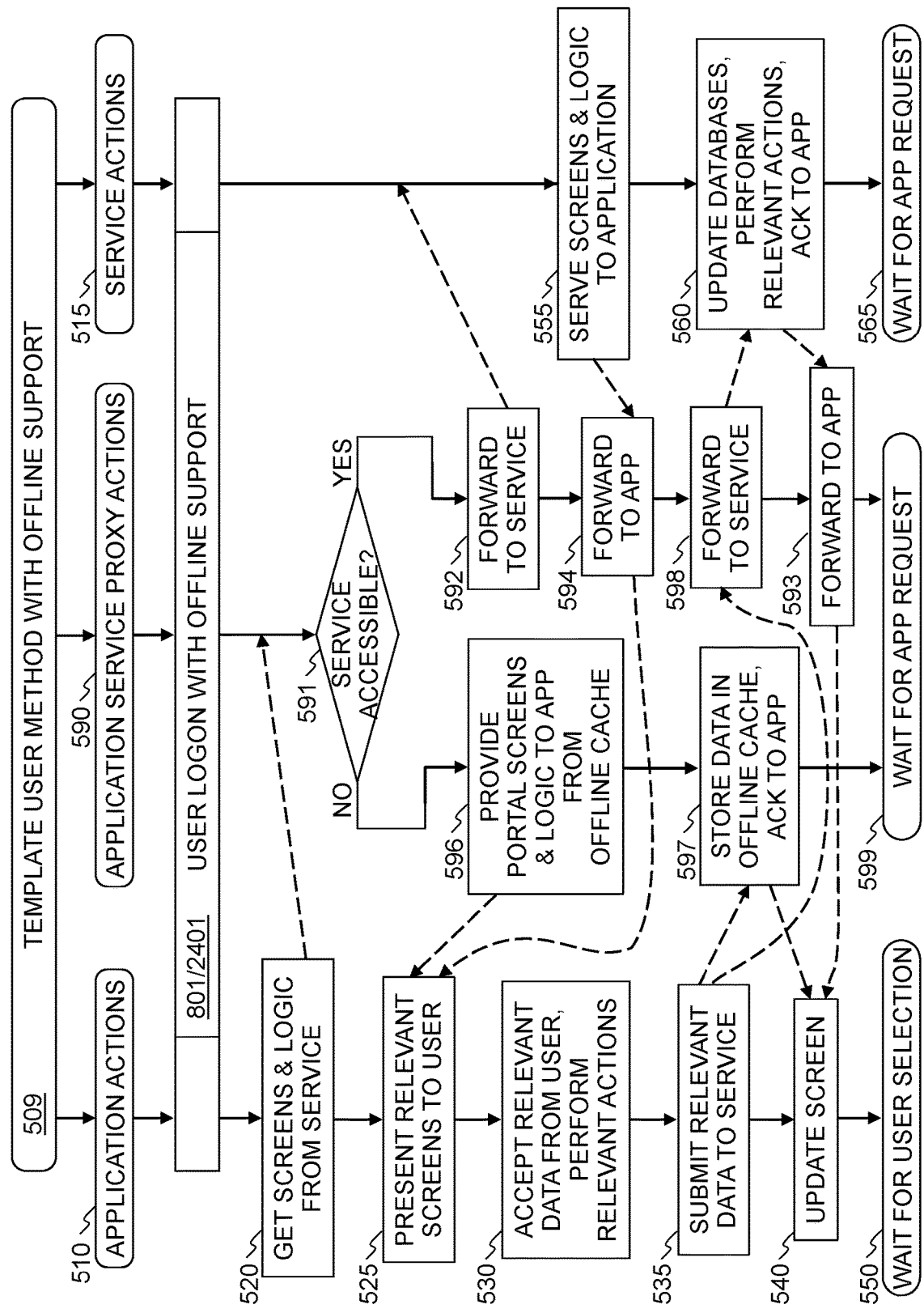

FIG. 9 depicts a template user method enhanced with offline support. This process template may be applied as a modification to every system method named in FIG. 5 and FIG. 22 of the base patent application to form the corresponding system methods with offline capability named in FIG. 5 and FIG. 6 of the present application. Four primary actors participate in this process template, and therefore in each of the methods to which it applies: a user, which may be either a patient or a clinician; an application, which may accordingly be the patient application 140 device app or the clinician application 150 web app; an application service proxy, which may accordingly be either patient portal service proxy 4240 or clinician portal service proxy 4250; and a service, which is the various elements of trial operations service suite 200, including in particular patient portal 204 or clinician portal 205 respectively. In the figure, the operations performed by three of these actors are shown as part of interacting sub-processes: application actions 510, application service proxy actions 590, and service actions 515. Application actions 510 and service actions 515 represent generalizations of the various application action and service action sub-processes of the various system methods to which this template process may be applied. The user is not represented in this figure due to space considerations, but the corresponding actions and interactions with application actions 510 may be identical to those of the various user action sub-processes of the various system methods to which this process template may be applied. The essence of this process template is the insertion of the service proxy into the flow in order to support offline operation of each applicable system method. As usual, solid arrows in the figure represent temporal ordering and information flow within a sub-process, and dashed arrows represent temporal ordering and information flow between sub-processes.

Template user method with offline support process 509 begins with the prerequisite of user logon with offline support process 801/2401, in which all four actors participate. After that, at operation 520 the application may request screens and logic from the service corresponding to the method selected by the user (not shown). The service proxy intercepts this request and at operation 591 checks whether the service is accessible or not using the result of the decision that was made during user logon with offline support process 801/2401.

If the application is online, at operation 592 the request may then be forwarded to the service, which in turn may serve the requested screens and logic to the application at operation 555. The service proxy may forward the response to the application at operation 594. If the application is offline, the service proxy may at operation 596 serve the requested screens and logic to the application from the offline cache. Note that if an item in operational data offline cache 4202 has been updated by another offline operation since the last successful synchronization, it may have created a conflict in the logic from the requested services cache. If this happens, the service proxy may if allowed by the cached logic make an assumption about the state of data in the service, proceed based on this assumption, and defer conflict resolution to the next synchronization. Alternatively, if cached logic dictates the service proxy may provide to the application an indication that offline operation cannot proceed, rather than providing the cached service screens and logic; this outcome is not depicted in the figure both for reasons of space and because it is expected to be a rare occurrence.

Whether offline or online, the application then at operation 525 presents the relevant screen or screens to the user, who in turn may perform associated actions such as entering data or making selections (not shown). The application may then at operation 530 accept the relevant data from the user and perform associated local actions as dictated by the service logic, and at operation 535 submit any relevant data to the service. The intervening service proxy may, if offline, at operation 597 operate on this data according to cached service logic, store it in operational data offline cache 4202, and return an acknowledgement to the application. If online, the service proxy may at operation 598 forward the data to the service, which may in turn at operation 560 update operational databases 202, perform relevant actions according to the service logic, and return an acknowledgement which is relayed by the service proxy to the application at operation 593. The application may then update its screen accordingly at operation 540.

At this point, template user method with offline support process 509 is complete, with each sub-process quiescing in its own way. The user sub-process (not shown) simply finishes, with nothing further for the user to do. In application sub-process 510, the application remains running in patient personal computing device 104 or clinician workstation 105, so its quiescent state is waiting for the user's next selection at operation 550 while the associated application service proxy quiesces waiting for the next application request at operation 599. Similarly, if the application is online—connected to and authenticated with the service— the corresponding portal 204 or 205 has an established session for the user, so it too quiesces in an active state waiting for the next application request at operation 565. Any of the other user methods may be selected in this state.

Figure 10A:
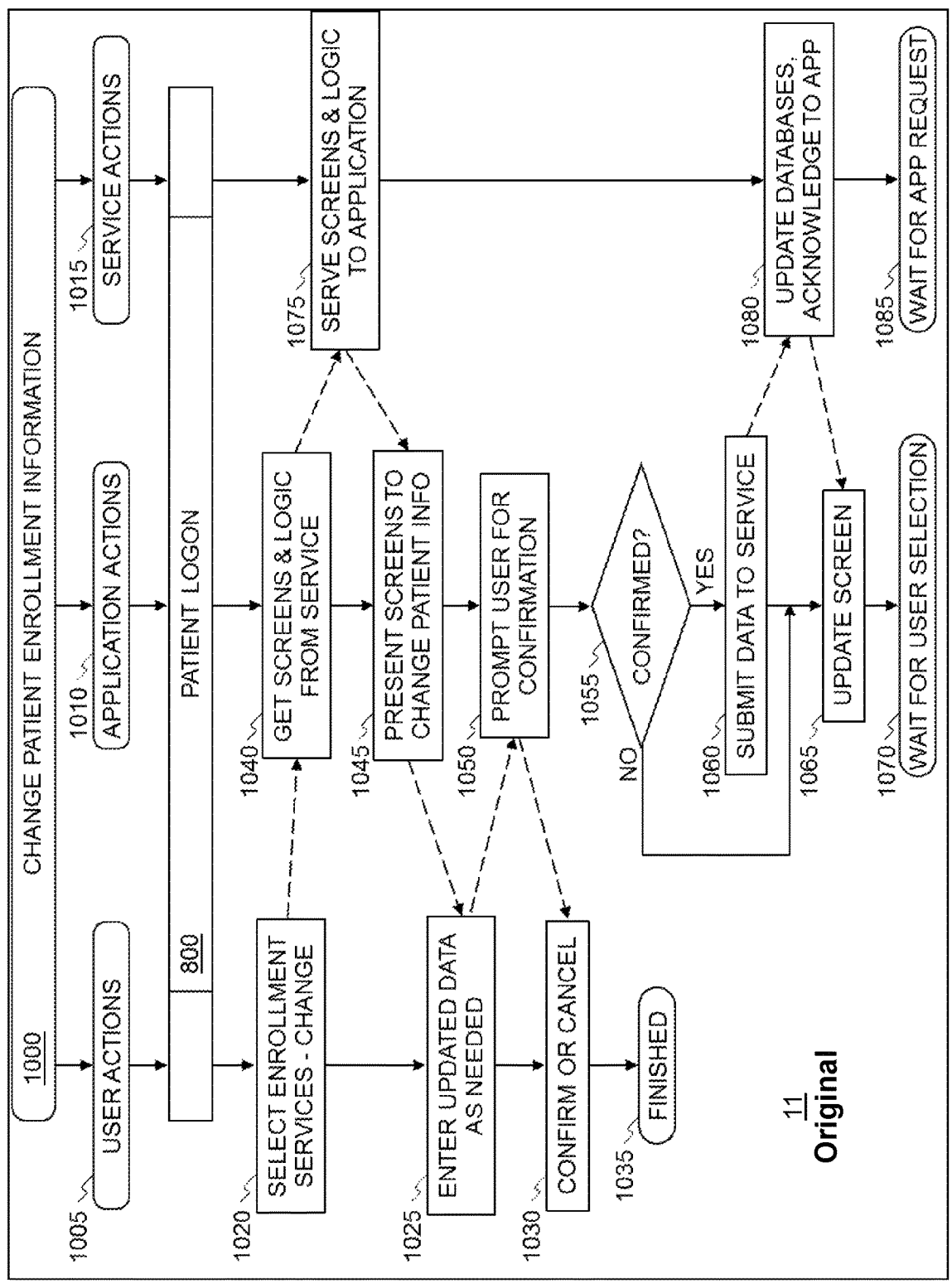
Figure 10B:
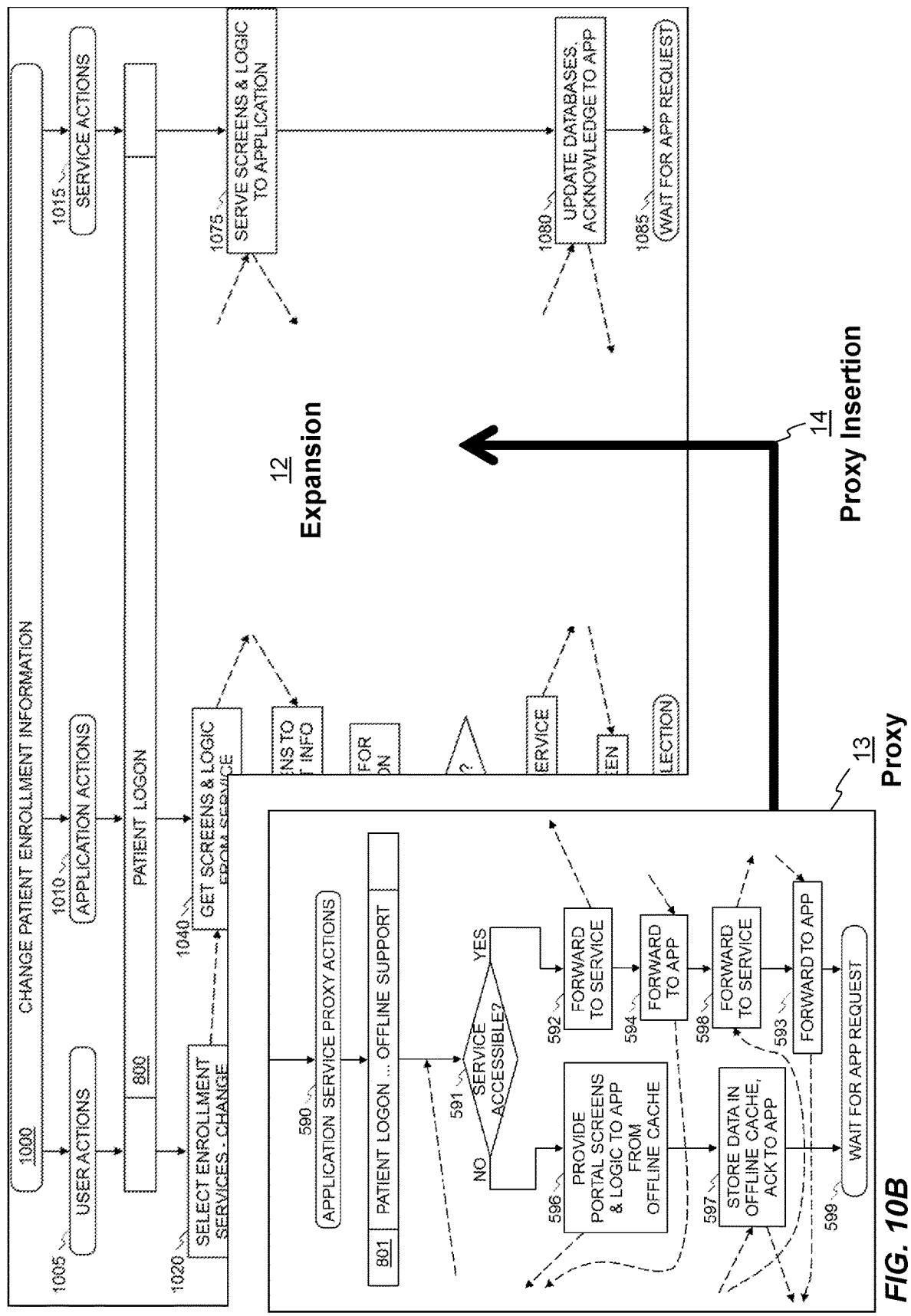
Figure 10C:
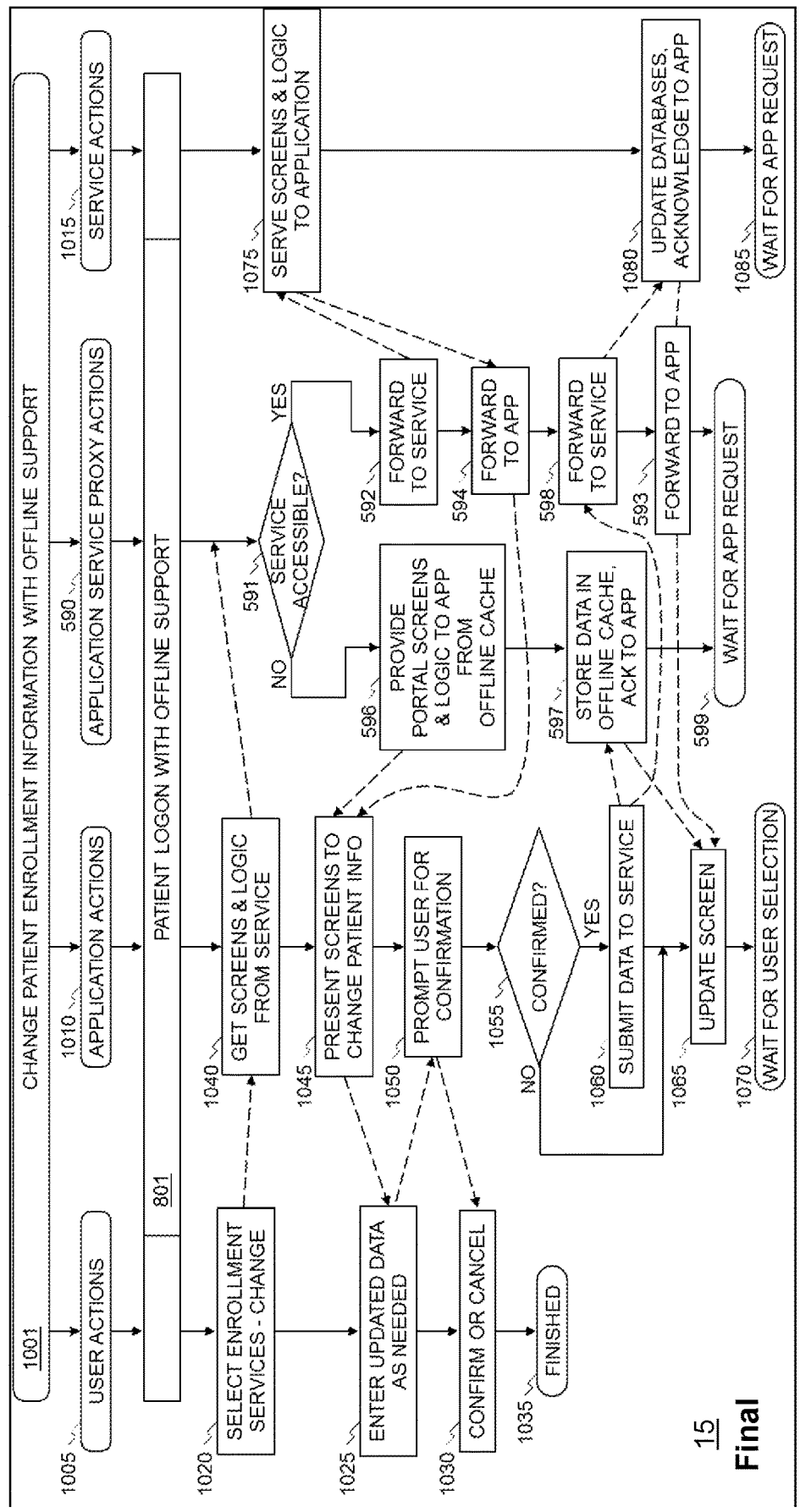

FIGS. 10A-C provide an example of applying the template user method with offline support process 509 to a process of the base patent application, in this case the change patient enrollment information process 1000. Change patient enrollment information process 1000 may be transformed into change patient enrollment information with offline support process 1001 by starting with the original process 11, performing an expansion 12 to make room for proxy sub-process 13, performing proxy insertion 14 and aligning the inter-sub-process arrows to produce final process 15. These operations are both graphical and textual. The graphical operation of proxy insertion 14 is effectively pasting in a block and aligning some arrow endpoints. The textual operation of proxy insertion 14 requires interleaving the actions in proxy 13 with the actions in original process 11 in the usual temporal order. Thus, both the diagrams and descriptions of the original process 11 and proxy sub-process 13 are combined to form final process 15. The corresponding description of change patient enrollment information with offline support process 1001 follows. Note that certain component designators may refer to components that are not shown in FIG. 2 of the present disclosure, where certain details have been omitted for concision; those components are shown explicitly in FIG. 2 and FIG. 3 of the base patent application and are therefore implied to be present here.

When a patient needs to change enrollment information, such as contact address or health status, or even to withdraw from the trial by deleting enrollment, the change patient enrollment information with offline support process 1001 may be used, as depicted in FIG. 10C. The same three-actor model applies here, with the same temporal/informational interaction conventions. The sub-processes in this case are labeled user actions 1005, application actions 1010, application service proxy actions 590, and service actions 1015.

Change patient enrollment information with offline support process 1001 begins with the prerequisite of patient logon with offline support process 801, in which all four actors participate. After that, at operation 1020 the patient may select the change option under enrollment services 241 from the menu of patient portal services 240. At operation 1040 patient application 140 may get the corresponding additional screens and logic from patient portal 204 if they are not already loaded. The service proxy intercepts this request and at operation 591 checks whether the service is accessible or not using the result of the decision that was made during patient logon with offline support process 801.

If the application is online, at operation 592 the request may then be forwarded to the service, which in turn may serve the requested screens and logic to the application at operation 1075. The service proxy may forward the response to the application at operation 594. If the application is offline, the service proxy may at operation 596 serve the requested screens and logic to the application from the offline cache. Note that if an item in operational data offline cache 4202 (FIG. 4) has been updated by another offline operation since the last successful synchronization, it may have created a conflict in the logic from the requested services cache. If this happens, the service proxy may if allowed by the cached logic make an assumption about the state of data in the service, proceed based on this assumption, and defer conflict resolution to the next synchronization. Alternatively, if cached logic dictates the service proxy may provide to the application an indication that offline operation cannot proceed, rather than providing the cached service screens and logic; this outcome is not depicted in the figure both for reasons of space and because it is expected to be a rare occurrence.

At operation 1045, then, the application presents the appropriate screens for changing enrollment information. Depending on the trial design established by a coordinator, the patient may be presented one or more screens of options and data entry opportunities in order to update the information as needed, all embodied in operation 1025. This may take the form of several interactions between user and app, but in the end when all the changes have been made, patient application 140 (FIG. 1) at operation 1050 may prompt the patient for confirmation, and the patient at operation 1030 may choose to confirm or cancel the changes. If patient application 140 determines at operation 1055 that the patient confirmed the changes, it may at operation 1060 submit the change package to patient portal 204 enrollment services 241 (FIG. 2).

The intervening service proxy may, if offline, at operation 597 operate on this data according to cached service logic, store it in operational data offline cache 4202, and return an acknowledgement to the application. If online, the service proxy may at operation 598 forward the data to the service, which in turn at operation 1080 would update operational databases 202 (FIG. 2) with this new information about the patient. Some of the information may be updated in provisioning and authorization data 222 (FIG. 2), while other information may be categorized such that it must be updated in protected health information 223 (FIG. 2); if appropriate, some of the latter may also be de-identified and recorded in anonymized health information 224 (FIG. 2). When all the data is safely stored, still within operation 1080, patient portal 204 enrollment services 241 should provide an acknowledgement to patient application 140 so it knows the change was successful, which is relayed by the service proxy to the application at operation 593. Confirmed or not, changed successfully or not, patient application 140 updates the screen to reflect the appropriate state of affairs at operation 1065.

At this point, change patient enrollment information with offline support process 1001 is complete, with each sub-process quiescing in its own way. User sub-process 1005 simply finishes at operation 1035, with nothing further for the patient to do. In application sub-process 1010, patient application 140 (FIG. 1) remains running in patient personal computing device 104, so its quiescent state is waiting for the user's next selection at operation 1070, while the associated application service proxy quiesces waiting for the next application request at operation 599. Similarly, if the application is online—connected to and authenticated with the service—patient portal 204 (FIG. 2) has an established session for this user, with patient application 140 connected and authenticated, so it too quiesces in an active state waiting for the next application request at operation 1085. Any of the other patient methods may be selected in this state.

As previously noted, the template user method with offline support process 509 may be applied to the pertinent processes in FIG. 5 and FIG. 22 of the base patent application to produce the processes in FIG. 5 and FIG. 6 of the present application. The operations of FIG. 10A-C may be used in each case to produce the corresponding diagram and description. Actually doing so for all the processes other than the exemplary transformation of change patient enrollment information process 1000 is a straightforward extrapolation for one skilled in the art.

The processes of FIG. 5 through FIG. 10C may be implemented in various different ways without departing from the scope of the disclosure. For instance, the operations may be performed in different orders than shown. As another example, some processes may include additional operations and/or omit various listed operations. While the examples shown may illustrate many individual modules (or operation sets, performed by software instructions and/or user, clinician, operator, etc. action) as separate elements, one of ordinary skill in the art would recognize that these modules may be combined into a single functional block or element. One of ordinary skill in the art would also recognize that a single module may be divided into multiple modules. Further, the steps, operation sets, functions, etc. described in the various modules are understood to be actionable via a computer or processor executing instructions, to provide the features and results described herein. Thus, one of ordinary skill in the computer and software arts, having read this disclosure, could devise and replicate the features of the various modules, as well as modifications within the scope of this disclosure without undue experimentation.

IV. Computer System

Many of the processes and modules described above may be implemented as software processes that are specified as one or more sets of instructions recorded on a non-transitory storage medium. When these instructions are executed by one or more computational element(s) (e.g., microprocessors, microcontrollers, digital signal processors (DSPs), application-specific integrated circuits (ASICs), field programmable gate arrays (FPGAs), etc.) the instructions cause the computational element(s) to perform actions specified in the instructions.

In some embodiments, various processes and modules described above may be implemented completely using electronic circuitry that may include various sets of devices or elements (e.g., sensors, logic gates, analog to digital converters, digital to analog converters, comparators, etc.). Such circuitry may be able to perform functions and/or features that may be associated with various software elements described throughout.

FIG. 78 in the base patent application illustrates a schematic block diagram of an exemplary computer system 7800 used to implement some embodiments. For example, the systems described above in reference to FIG. 1-FIG. 4 may be at least partially implemented using computer system 7800. As another example, the processes described in reference to FIG. 5-FIG. 10C may be at least partially implemented using sets of instructions that are executed using computer system 7800.

Computer system 7800 may be implemented using various appropriate devices. For instance, the computer system may be implemented using one or more personal computers (PCs), servers, mobile devices (e.g., a smartphone), tablet devices, and/or any other appropriate devices. The various devices may work alone (e.g., the computer system may be implemented as a single PC) or in conjunction (e.g., some components of the computer system may be provided by a mobile device while other components are provided by a tablet device).

FIG. 78 of the base patent application and computer system 7800 are considered to be incorporated in the present patent application by reference, and therefore are not detailed here.

As used in this specification and any claims of this application, the terms "computer", "server", "processor", and "memory" all refer to electronic devices. These terms exclude people or groups of people. As used in this specification and any claims of this application, the term "non-transitory storage medium" is entirely restricted to tangible, physical objects that store information in a form that is readable by electronic devices. These terms exclude any wireless or other ephemeral signals.

It should be recognized by one of ordinary skill in the art that any or all of the components of computer system 7800 may be used in conjunction with some embodiments. Moreover, one of ordinary skill in the art will appreciate that many other system configurations may also be used in conjunction with some embodiments or components of some embodiments.

In addition, while the examples shown may illustrate many individual modules as separate elements, one of ordinary skill in the art would recognize that these modules may be combined into a single functional block or element. One of ordinary skill in the art would also recognize that a single module may be divided into multiple modules.

The foregoing relates to illustrative details of exemplary embodiments and modifications may be made without departing from the scope of the disclosure as defined by the following claims.

What is claimed is:

1. A system, comprising:
   one or more health monitoring sensors;
   one or more computational elements; and
   a non-transitory storage medium including instructions executable by the one or more computational elements to configure the one or more computational elements to:
      provide patient-directed access to clinical trial operation services;
      provide a clinician portal providing clinician-directed access to the clinical trial operation services;
      provide a trial design service configured to design, create, establish, deploy, or any combination thereof, a trial protocol and a participant interaction procedure using a flowable-based workflow palette in conjunction with visual programming, the flowable-based workflow palette including workflow attributes selectively indicating offline-capable procedures for a user interface for a clinical portal-supporting application as available offline;
      access, using the workflow attributes, workflows and screens from a service cache as needed for execution by a portal service proxy for the clinical portal-supporting application while offline;
      synchronize, when online, for a plurality of the offline-capable procedures, information collected using the workflow attributes while the clinical portal-supporting application is offline, wherein the information includes newly created data items stored in an operational data offline cache, wherein synchronization for the plurality of the offline-capable procedures is responsive to an invocation of a synchronization procedure by one of the offline-capable procedures;
      resolving data conflicts during the synchronization by sending a notification to a coordinator with appropriate privileges to resolve a conflict;
      receive acknowledgement of the newly created data items; and
      flush, in response to the acknowledgement, the newly created data items from the operational data offline cache.

2. The system of claim 1, wherein synchronizing when online comprises synchronizing information between the clinician portal and a clinician application when the clinician application is online to a server.

3. A system, comprising:
   one or more computational elements; and
   a non-transitory storage medium including instructions executable by the one or more computational elements to configure the one or more computational elements to:
      provide a user interface and network interface modules;
      provide user enrollment, user notification, user secure communication, user engagement, and user data capture service modules;
      provide a trial design service configured to design, create, establish, deploy, or any combination thereof, a trial protocol and a participant interaction procedure using a flowable-based workflow palette in conjunction with visual programming, the flowable-based workflow palette including workflow attributes selectively indicating offline-capable procedures for a user interface for a clinical portal-supporting application configured to collect sensor data from one or more health monitoring sensors as available offline using an offline portal proxy and data caches, allowing the clinical portal-supporting application to continue operating when offline from a server running a clinical trial operations service suite;

provide, using the workflow attributes, workflows and screens from a service cache from among the data caches as needed for execution by the offline portal proxy while offline; and provide a synchronization capability, including synchronizing, for a plurality of the offline-capable procedures, the sensor data from an operational data offline cache from among the data caches between the offline portal proxy and the clinical trial operations service suite, resolving data conflicts during the synchronization by sending a notification to a coordinator with appropriate privileges to resolve a conflict, and subsequently flushing the sensor data from the operational data offline cache in response to an acknowledgement when online with the server, wherein synchronization for the plurality of the offline-capable procedures is responsive to an invocation of a synchronization procedure by one of the offline-capable procedures.

4. The system of claim 3, wherein the instructions further configure the one or more computational elements to:

proxy a patient portal of the clinical trial operations service suite, the proxied patient portal comprising:
a patient logon screen for a clinical trial;
a patient enrollment menu for the clinical trial;
an invitation option for at least one of another patient or a clinician candidate to join the clinical trial;
a messaging-oriented communication option to securely communicate with other clinical trial participants upon reestablishment of an online state; and
health information specific goals of the clinical trial, wherein inputted information to the proxied patient portal is saved for online synchronization with the clinical trial operation service suite.

5. The system of claim 4, wherein:
the clinical portal-supporting application includes a clinician application running on a clinician-located computer; and
the offline portal proxy proxies a clinician portal of the clinical trial operations service suite, the proxied clinician portal comprising:
a clinician logon screen for a clinical trial;
a clinician enrollment menu for the clinical trial;
an invitation option for at least one of another patient or a clinician candidate to join the clinical trial, and a tracking status of an invitation;
a messaging-oriented communication option to securely communicate with other clinical trial participants upon reestablishment of the online state; and
health information specific goals of the clinical trial, wherein inputted information to the proxied clinician portal is saved for online synchronization with the clinical trial operation service suite.

6. The system of claim 4, further comprising, a display interface for at least one of a patient survey query, a schedule of patient events, or a patient-recorded record of observations.

7. The system of claim 5, further comprising, a display interface for at least one of a screen allowing a clinician to compose and send a notification, a clinician survey query, a schedule of clinician events, or a clinician-recorded record of observations.

8. The system of claim 5, wherein the one or more health monitoring sensors comprise a clinician-operated health sensor.

9. A method of operating a trial operations service suite in a clinical trial operations system, comprising:

producing a trial protocol and a participant interaction procedure using a flowable-based workflow palette in conjunction with visual programming, the flowable-based workflow palette including workflow attributes selectively indicating offline-capable procedures for a user interface for a clinical portal-supporting application as available offline;

running trial operations service suite software on a computer, the trial operations service suite software incorporating the trial protocol and the participant interaction procedure;

communicating with a user application running on a user device;

displaying, based on the workflow attributes and using workflows and screens from a service cache in the computer as needed while the clinical portal-supporting application is offline, at least one of a service screen or the user interface on the user device, the user interface querying for user input for use in a clinical trial;

receiving the user input on the user device;

synchronizing when online with the computer, service suite information, service screen logic, sensor data received from one or more health monitoring sensors and stored in an operational data offline cache of the user device, and information from the user input including the information from a plurality of offline-capable procedures for a user interface for the clinical portal-supporting application that are available offline by using the service cache, collected by the user application when the user application is offline from the computer, wherein synchronization for the plurality of the offline-capable procedures is responsive to an invocation of a synchronization procedure by one of the offline-capable procedures;

resolving data conflicts during the synchronization by sending a notification to a coordinator with appropriate privileges to resolve a conflict;

sending an acknowledgement of the sensor data from the computer to the user device; and flushing, in response to the acknowledgement, the sensor data from the operational data offline cache.

10. The method of claim 9, further comprising, when a data conflict arises during synchronization, wherein the user application conflicts with the trial operations service suite since a previous synchronization, the trial operations service suite assumes new data overrides old data and continues synchronizing.

11. The method of claim 10, further comprising, the trial operations service suite notifying a coordinator to manually resolve the data conflict.

12. The method of claim 10, further comprising, applying an analytic module associated with the trial operations service suite to autonomously resolve the data conflicts.

13. The method of claim 9, wherein the user application is a patient application and the trial operations service suite provides a patient portal.

14. The method of claim 9, wherein the user application is a clinician application and the trial operations service suite provides a clinician portal.

15. A method of operating an application in a clinical trial operations system, comprising:

producing a trial protocol and a participant interaction procedure using a flowable-based workflow palette in conjunction with visual programming, the flowable-based workflow palette including workflow attributes selectively indicating offline-capable procedures for a user interface for the application as available offline;

when the application is connected to a portal of a trial operations service suite, synchronizing, for a plurality of the offline-capable procedures, portal and application data, service screens and logic, and offline data collected by the application while not connected based on the workflow attributes selectively indicating the offline-capable procedures for the user interface for the application as available offline, wherein synchronization for the plurality of the offline-capable procedures is responsive to an invocation of a synchronization procedure by one of the offline-capable procedures;

resolving data conflicts during the synchronization by sending a notification to a coordinator with appropriate privileges to resolve a conflict; and when the application is not connected to the portal, using a proxy embedded in the application to continue providing service and collecting the offline data according to previously synchronized portal data, service screens, and service logic, based on the workflow attributes selectively indicating the offline-capable procedures for the user interface for the application as available offline from a service cache, wherein the offline data includes sensor data from health monitoring sensors stored in an operational data offline cache while the application is available offline;

wherein the synchronizing of the portal and application data includes sending an acknowledgement of the sensor data from the portal of the trial operations service suite to the application and flushing, in response to the acknowledgement, the sensor data from the operational data offline cache.

16. The method of claim 15, further comprising, when a data conflict arises during offline operation, wherein the application either requires portal data that is not available or depends on portal data that has changed while offline in such a manner as to be inconsistent with a cached service logic, the proxy stops supporting the service while offline.

17. The method of claim 15, further comprising, when a data conflict arises during offline operation, wherein the application either requires portal data that is not available or depends on portal data that has changed while offline in such a manner as to be inconsistent with a cached service logic, the proxy assumes new data overrides old data and continues supporting the service while offline.

18. The method of claim 15, wherein the application is a patient application and the portal is a patient portal.

19. The method of claim 15, wherein the application is a clinician application and the portal is a clinician portal.

\* \* \* \* \*